(12) United States Patent
Khan et al.

(10) Patent No.: US 7,595,326 B2
(45) Date of Patent: Sep. 29, 2009

(54) SYNTHESIS OF NOVEL TUBULIN POLYMERIZATION INHIBITORS: BENZOYLPHENYLUREA (BPU) SULFUR ANALOGS

(75) Inventors: Saeed R. Khan, Owings Mills, MD (US); Gurulinsappa Hallur, Owings Mills, MD (US); Manuel Hidalgo, Baltimore, MD (US); Antonio Jimeno, Baltimore, MD (US)

(73) Assignee: Champions Biotechnology, Inc., Tempe, AZ (US)

( * ) Notice: Subject to any disclaimer, the term of this patent is extended or adjusted under 35 U.S.C. 154(b) by 0 days.

(21) Appl. No.: 11/673,519

(22) Filed: Feb. 9, 2007

(65) Prior Publication Data

US 2007/0232631 A1 Oct. 4, 2007

Related U.S. Application Data

(63) Continuation of application No. PCT/US06/14449, filed on Apr. 18, 2006.

(60) Provisional application No. 60/720,755, filed on Sep. 27, 2005, provisional application No. 60/696,672, filed on Jul. 5, 2005, provisional application No. 60/672,469, filed on Apr. 18, 2005.

(51) Int. Cl.
*C07D 239/38* (2006.01)
*A61K 31/505* (2006.01)
*A61P 35/00* (2006.01)

(52) U.S. Cl. ...................... 514/269; 544/316
(58) Field of Classification Search ................ 544/316; 514/269
See application file for complete search history.

(56) References Cited

OTHER PUBLICATIONS

Wood et al., Current Opinion in Pharmacology, 1, 370-377, 2001.*
Andoh et al., Advances in Pharmacology, 29B, 93-103, 1994.*
Denny et al., Expert Opin. Emerg. Drugs, 9(1), 105-133, 2004.*
Ruchelman et al., Biorganic & Medicinal Chemistry, 12, 795-806, 2004.*
Cecil Textbook of Medicine, edited by Bennet, J.C., and Plum F., 20th edition, vol. 1, 1004-1010, 1996.*
Downing, K. H. et al , "Tubulin Structure: Insights into Microtubule Properties and Functions" Current Opininion in Structural Biology, 1988,:785-791.
Sorger P. K., et al "Coupling Cell Division and Cell Death to Microtubule Dynamics" Curr. Opin. Cell Biol, vol. 9:807-814 (1997).
Jordan A. et al "Tubulin as a Target for Anticancer Drugs:Ageents Which Interact with the Mitotic Spindle" *Med. Res. Rev.*, vol. 18 No. 4, 259-296 (1998).
Lehnert, M. "Clinical Multidrug Resistance in Cancer: A Multifactorial Problem" European Journal of Cancer vol. 32A, No. 6, pp. 912-921 (1996).
Germann U.A. "P-glycoprotein-A Mediator of Multidrug Resistance in Tumour Cells", Eruopean Journal of Cancer, vol. 32A, No. 6, pp. 927-944, (1996).
Easmon, J. et al. "Synthesis, Cytotoxiity, and Antitumor Activity of Copper (II) and Iron (II) Complexes of N-Azabicyclo[3.3.3.] nonane Thiosemicarbazones Derived from Acyl Diazines" Journal of Medicinal Chemistry, 2001, 44 (13):2164-2171.
Jordan A M. et al Synthesis and Analysis of Urea and Carbamate prodrugs as Candidatges for Melanocyte-Directed Enzyme Prodrug Therapy (MDEPT), Bioorganic and Medicinal Chemistry, vol. 10:2625.
Okada, H. et al "Synthesis and Antitumor Activities of Novel Benzoylphenylurea Derivatives", Chem. Pharm. Bull., vol. 39 No. 9:2308-2315 (1991).
Okada, H., et al "Synthesis and Antitumor Activities of Prodrugs of Benzolyphenylureas", Chem. Pharm. Bull., vol. 42 No. 1:57-61 (1994).
Okada, H. et al "Synthesis and Antitumor Activities of Water-Soluble Benzolphenylureas", Chem. Pharm. Bull., vol. 47, No. 3:430-433 (1999).
Holligshead, M. G., et al Immunochemistry of Suppressor Substances, Proc. Am. Assoc. Cancer Res., 39:164 (1979).
Messersmith W. A. et al "Phase I study of continuous weekly dosing of dimethyl benzoylphenylurea (BPU) in patients with solid tumors" Proc. Am. Soc. Clin. Oncol, vol. 22:203 (2003).
Brophy T.R. et al "Bioavailability of Oral Dexamethasone During High Dose Steriod Therapy in Neurological Patients" European Journal of Clinical Pharmacology, 1983 24:103-108.
Chonn A et al "Recent Advances in Liposomal Drug-Delivery Systems", Current Opinion in Biotechnology, 6:698-708 (1995).
Johnson M. E. et al "Permeation of Steriods through Human Skin", *J. Pharm. Sci.*, vol. 841:1144-1146 (1995).
Edelman M. J. et al "Phase I, Pharmacokinetic (PK) and Pharmacodynamic Study Benzoylphenylurea (BPU, NSC 639829), a Novel Antitubulin Agent" Proc. Am. Soc. Clin. Oncol, vol. 22:137 (2003).
Gurulingappa H. et al, Synthesis and Antitumor Evaluation of Benzoylphenylurea Analogs Bioorganic + Medicinal Chemistry Letters, 14:2213-2216 (2004).
Berge S.M et al "Pharmaceutical Salts", Journal of Pharmaceutical Science, 1977, vol. 66, No. 1.
Mosmann T. "Rapid Colorimetric Assay for Cellular Growth and Survivial: Application to Proliferation and Cytotoxicity Assays" J. Immunol. Methods, vol. 65:55-63 (1983).
Hamel, E. "Evaluation of Antimitotic Agents by Quantitative Comparisons of Their Effects on the Polymerization of Purified Tubulin", Cell Biochem. Biophys., 38:1-22 (2003).

(Continued)

*Primary Examiner*—Venkataraman Balasubramanian
(74) *Attorney, Agent, or Firm*—Mark S. Cohen; Pearl Cohen Zedek Latzer, LLP

(57) ABSTRACT

A novel series of BPU analogues were synthesized and evaluated for antitumor activity. In particular, BPU sulfur analogues 6n and 7d were shown to possess up to 10-fold increased potency, when compared to compound 1, against cancer cell lines. 6n was more effective than compound 1 in causing apoptosis of MCF-7 cells. When compared to other drugs with a similar mechanism of action, 6n retained significant ability to inhibit tubulin assembly, with an $IC_{50}$ of 2.1 μM.

12 Claims, 21 Drawing Sheets

OTHER PUBLICATIONS

Verdier-Pinard P. et al "Structure-Activity Analysis of the Interaction of Curacin A, the Potent Colchicine Site Antimitotic Agent, with Tubulin and Effects of Analogs on the Growth of MCF-7 Breast Cancer Cells" Mol Pharmacol, vol. 53:62-76 (1998).

Rohatagi S. et al "Phamracokinetic and Pharmacoynamic evaluation of Triamcinolone Acetonide after Intravenous, Oral, and Inhaled Administration", The Jhouranl of Clinical Pharmacology, vol. 35 : 1187-1193, 1995.

Minto C. F. et al "Pharmacokinetcs and Pharmacodynamics of Nandrolone Esters in Oil Vehicle: Effects of Ester, Injection Site and Injection Volume" J. Pharmacol. Exp. Ther., vol. 281, No. 1, :93-102 (1997).

Panduranga Rao K. "Recent Developments of Collagen-Based materials for Medical Applications and Drug Delivery Systems", J. Biomater Sci. Polym. Ed., vol. 7:623-645 (1995).

Gao Z-H. et al "Controlled Release of a Contraceptive Steoid from Biodegradable and Injectabl gel Formulations: In Vitro Evaluation" Pharmaceutical Research, vol. 12:857-863 (1995).

Eyles J.E. et al "Oral Delivery and Fate of Poly(lactic acid) Microsphere-encapsulated Interferon in Rats", *J. Pharm. Pharmacol*, 49:669-674 (1997).

Fotherby K "Bioavailability of Orally Adminstrated Sex Steroids used in Oral Contraception and Hormone Replacement Therapy" Contraception, 1996, 54:59-69.

Hidalgo-Aragones M.I. et al "Pharmacokinetics of Oestrone-3-0-Suplhamate" *J. Steroid Biochem. Mol. Biol*, vol. 58:611-617 (1996).

Ostro M. J et al "Use of Lipsomes as Injectable-Drug Delivery Systems", American Journal of Hospital Pharmacy, vol. 46:1576-1587 (1989).

Tjwa M.K.T. "Budesonide Inhaled via Turbuhaler: A more Effective Treatment for Asthma than Beclomethasone Depropionate via Rotahaler", *Ann. Allergy Asthma Immunol.* 75:107-111, (1995).

* cited by examiner

SYNTHESIS OF NOVEL TUBULIN POLYMERIZATION INHIBITORS: BENZOYLPHENYLUREA (BPU) SULFUR ANALOGS

CROSS-REFERENCES TO RELATED APPLICATIONS

This application is a continuation of PCT/US2006/014449, filed Apr. 18, 2006 and published as WO 2006/113650, which claims benefit of priority from U.S. Provisional Patent Application Nos. 60/672,469, filed Apr. 18, 2005; 60/696,672 filed Jul. 5, 2005; and 60/720,755 filed Sep. 27, 2005. All four applications are incorporated herein by reference in their entireties for all purposes.

STATEMENT AS TO RIGHTS TO INVENTIONS MADE UNDER FEDERALLY SPONSORED RESEARCH OR DEVELOPMENT

This study was supported in-part by National Cancer Institute Contract #NO1-CO-12400 and all joint inventors have assigned their rights to Johns Hopkins University.

BACKGROUND OF THE INVENTION

1. Field of Invention

The present invention relates to design and synthesis of novel benzoylphenylurea (BPU) sulfur analogs with increased potency and enhanced water solubility. More specifically, the present invention is directed toward the synthesis of sulfur, hydroximic acid, and boronic acid analogs of BPU.

2. Brief Description of Art

The lack of selectivity of many cancer agents and the occurrence of intrinsic or acquired resistance of tumors to chemotherapy have been major obstacles in the treatment of cancer. Microtubules, which are key components of the cell, play an important role in a variety of cellular process, including mitosis and cell division. See, Downing, K. H., et al., Curr. Opin. Struct. Biol., 8:785-791 (1998) and Sorger, P. K., et al., Curr. Opin. Cell Biol., 9:807-814 (1997). Antimitotic agents can be divided into two major classes: (1) microtubule stabilizers such as paclitaxel and docetaxel, which prevent the depolymerization of tubulin (Jordan, A., et al., Med. Res. Rev., 18:259-296 (1998)); and (2) Vinca alkaloids (e.g., vincristine, vinblastine, and vinorelbine) and colchicines, which inhibit the polymerization of tubulin (Jordan, A., et al., Med. Res. Rev., 18:259-296 (1998)). Although some of these agents have been used as antiproliferative agents in the treatment of human malignancies, they suffer from drug resistance mediated through the expression of efflux pumps. See, Lehnert, M., Eur. J. Cancer, 32A:912-920 (1996) and Germann, U. A., Eur. J. Cancer, 32A:927-944 (1996).

Urea and thiourea derivatives have been used for the treatment of a wide range of solid tumors, Easmon, J. et al.; J. Med. Chem., 44:2164-2171 (2001). Urea-based prodrugs have been reported as candidates for melanocyte-directed enzyme prodrug therapy (MDEPT), in which they release the drug upon exposure to tyrosinase. See, Jordan, A. M. et al., Bioorg. Med. Chem., 10:2625-2633 (2002). Benzoylphenylurea (BPU) compounds were originally developed as insecticides, and their antitumor activity was found during random screening (Okada, H., et al., Chem. Pharm. Bull., 39:2308-2315 (1991)). Various analogues of BPU were synthesized, and their cytotoxic activity was examined to establish structure-activity relationships (Okada, H., et al, Chem. Pharm. Bull., 39:2308-2315 (1991)). To improve physicochemical properties, organic and water soluble BPU derivatives were developed. See, Okada, H., et al., Chem. Pharm. Bull., 42:57-61 (1994); and Okada, H., et al., Chem. Pharm. Bull., 47:430-433 (1999). Six of these analogues were screened at the NCI for their cytotoxicity against various cancer cell lines. They exhibited potent antitumor activity in vitro against several cancer cell lines, as well in vivo against several tumor models. These compounds also have been reported to be effective inhibitors of tubulin polymerization (Holligshead, M. G., et al., Proc. Am. Assoc. Cancer Res., 39:164 (1979)). One of these agents, compound 1 (NSC-639829),

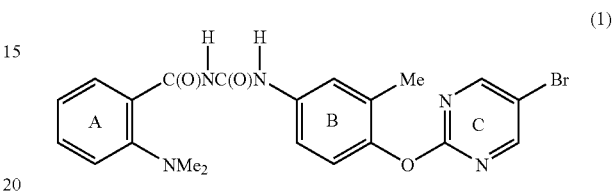

(Holligshead, M. G., et al, Proc. Am. Assoc. Cancer Res., 39:164 (1979)) is currently being evaluated in Phase I clinical trials in patients with refractory metastatic cancer. See, Messersmith, W. A., et al., Proc. Am. Soc. Clin. Oncol., 22:203 (2003); and Edelman, M. J., et al., Proc. Am. Soc. Clin. Oncol., 22:137 (2003). We have previously reported the synthesis and antitumor evaluation of a set of BPU analogues (Gurulingappa, H., et al., Bioorg. Med. Chem. Lett., 14:2213-2216 (2004)).

There is still a need to improve physicochemical properties, organic and water soluble BPU derivatives. To that end the present invention discloses a novel series of synthesized derivatives of BPU by replacing the urea moiety with thiourea and the ether linkage with sulfide, sulfoxide, or sulfone groups. The activity of such novel agents, are significantly more toxic to cancer cells in culture.

BRIEF SUMMARY OF THE INVENTION

In one aspect, the present invention provides an antiproliferative, water soluble compound with high bioavailability having the general formula (I)

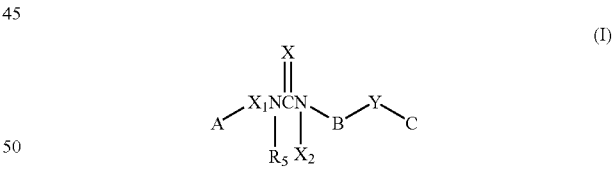

where A, B, and C are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur; 'Y' is sulfur, sulfoxide or sulfone; $X_1$ is CO or hydrogen; $R_5$ is hydrogen, or alkyl or aryl group; $X_2$ is hydrogen or $SR_6$, wherein $R_6$ is a substituted alkyl, cycloalkyl, aryl, heterocycle, or substituted phenyl fused with a saturated or unsaturated 4- to 6-membered rings optionally containing one to three heteroatoms independently selected from N, O, and S.

In another aspect, the present invention provides pharmaceutical compositions. The pharmaceutical composition includes a pharmaceutically acceptable excipient and a compound having the formula (I):

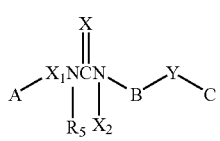

(I)

where A, B, and C are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur; 'Y' is sulfur, sulfoxide or sulfone; $X_1$ is CO or hydrogen; $R_5$ is hydrogen, or alkyl or aryl group; $X_2$ is hydrogen or $SR_6$, wherein $R_6$ is a substituted alkyl, cycloalkyl, aryl, heterocycle, or substituted phenyl fused with a saturated or unsaturated 4- to 6-membered rings optionally containing one to three heteroatoms independently selected from N, O, and S.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In the drawings, FIGS. 8-16, the cytotoxic effects of the test compounds on seven pancreatic cell lines was measured. The horizontal axis depicts various dilutions of the test compounds that were exposed to pancreatic cell lines. The vertical axis (cell number) depicts the number of pancreatic cells present after exposure to a specific concentration of the tested compound as compared to the cell number at time zero.

Figure 1:
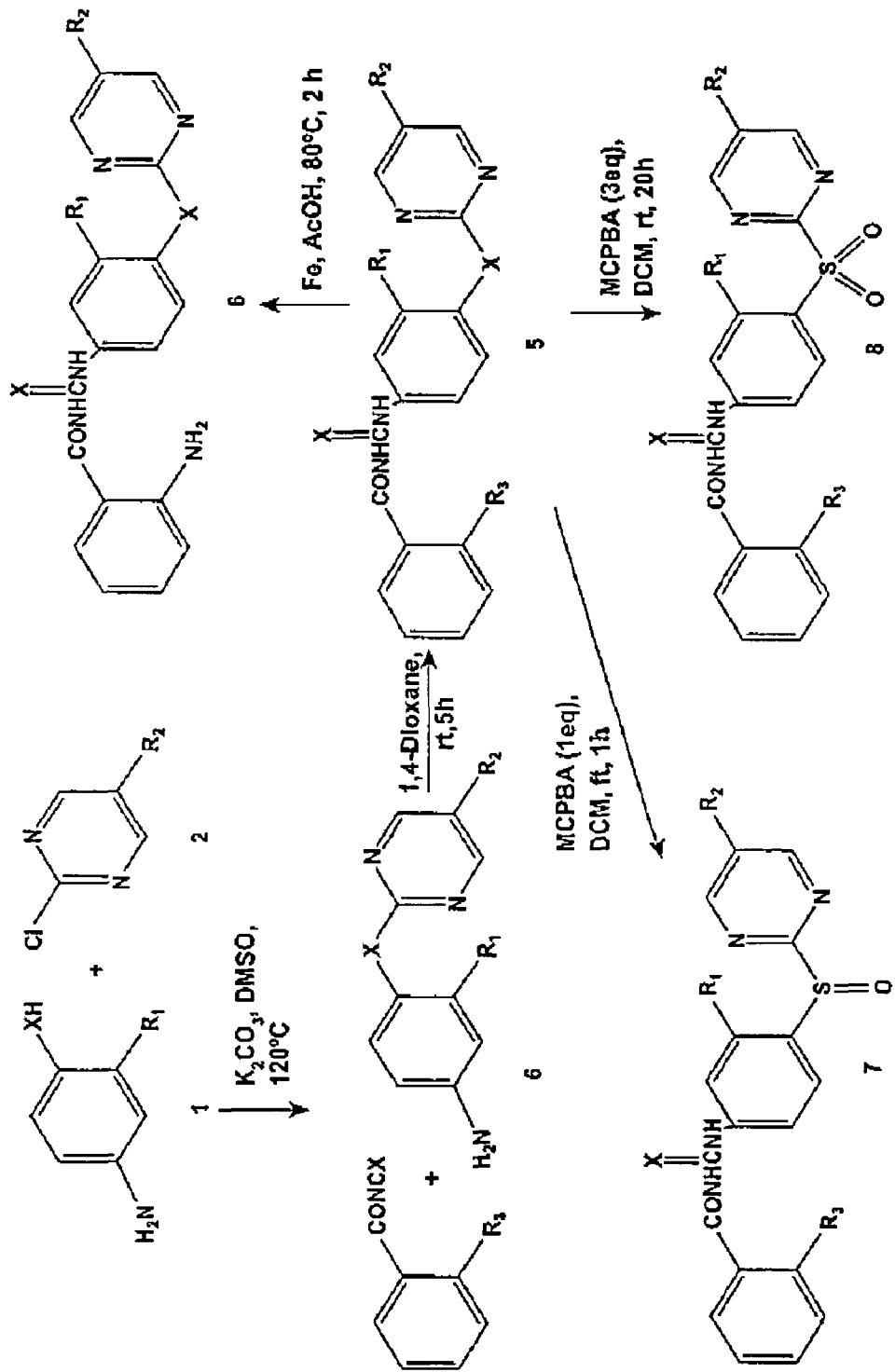

In the drawings, FIGS. 17-34, the growth inhibition effects of the test compounds on prostate cancer cell lines LAPC-4 (FIGS. 10-15); CWR22R (FIGS. 16-21); and LnCaP (FIGS. 22-27) are measured. The horizontal axis depicts the days after exposure on which the assays were performed. The vertical axis (cell number) depicts the number of pancreatic cells present after exposure to a specific concentration of the tested compound as compared to the cell number at time zero.

In the Drawings:

FIG. 1 schematically depicts the synthesis scheme for compounds of the present invention.

Figure 2:
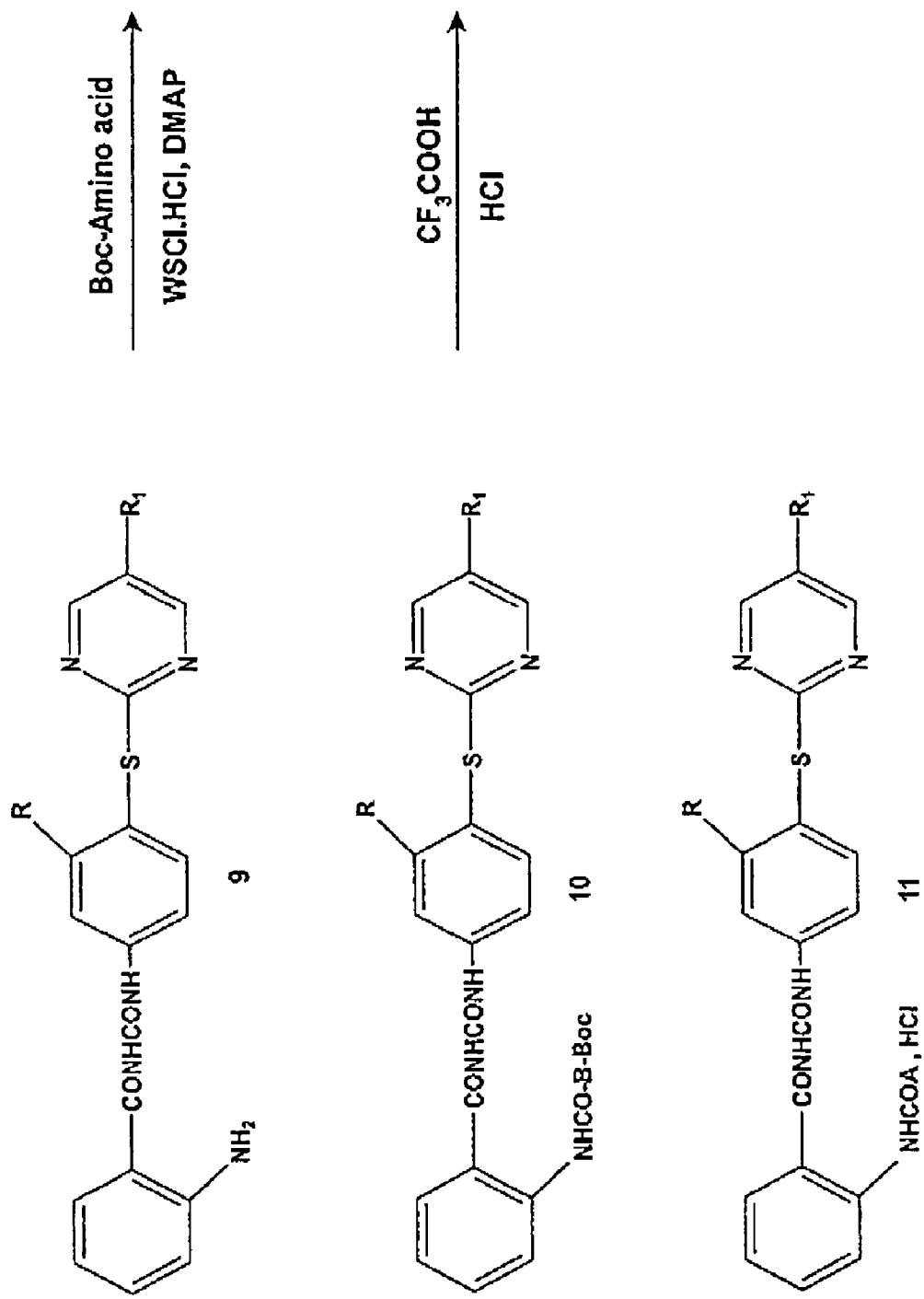

FIG. 2 schematically depicts the synthesis of the Ring-A aniline modified amino acids prodrugs.

Figure 3:
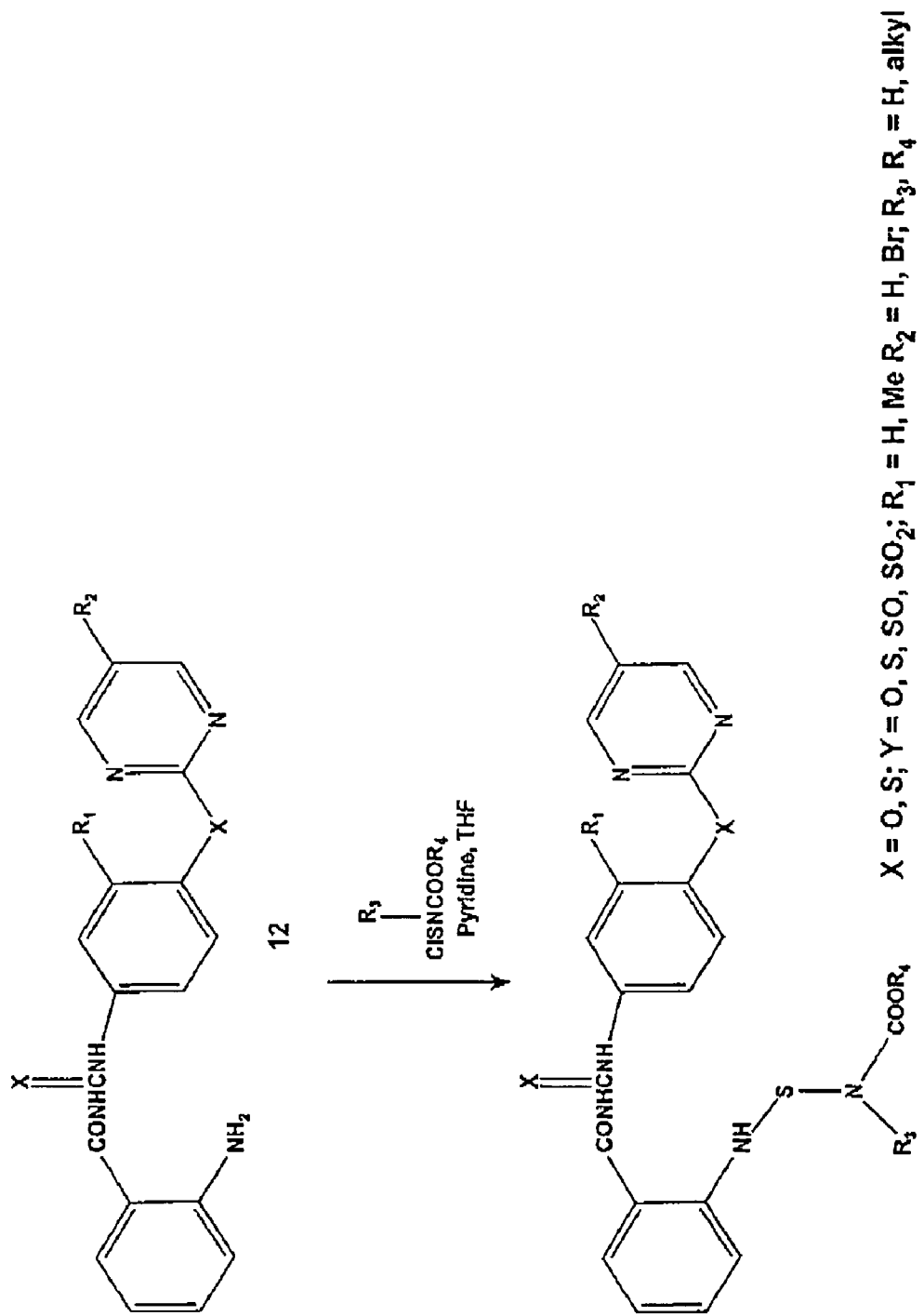

FIG. 3 schematically depicts the synthesis scheme for ring-A aniline modified carbamylosulfenyl derivative of BPU sulfur analogs.

Figure 4:
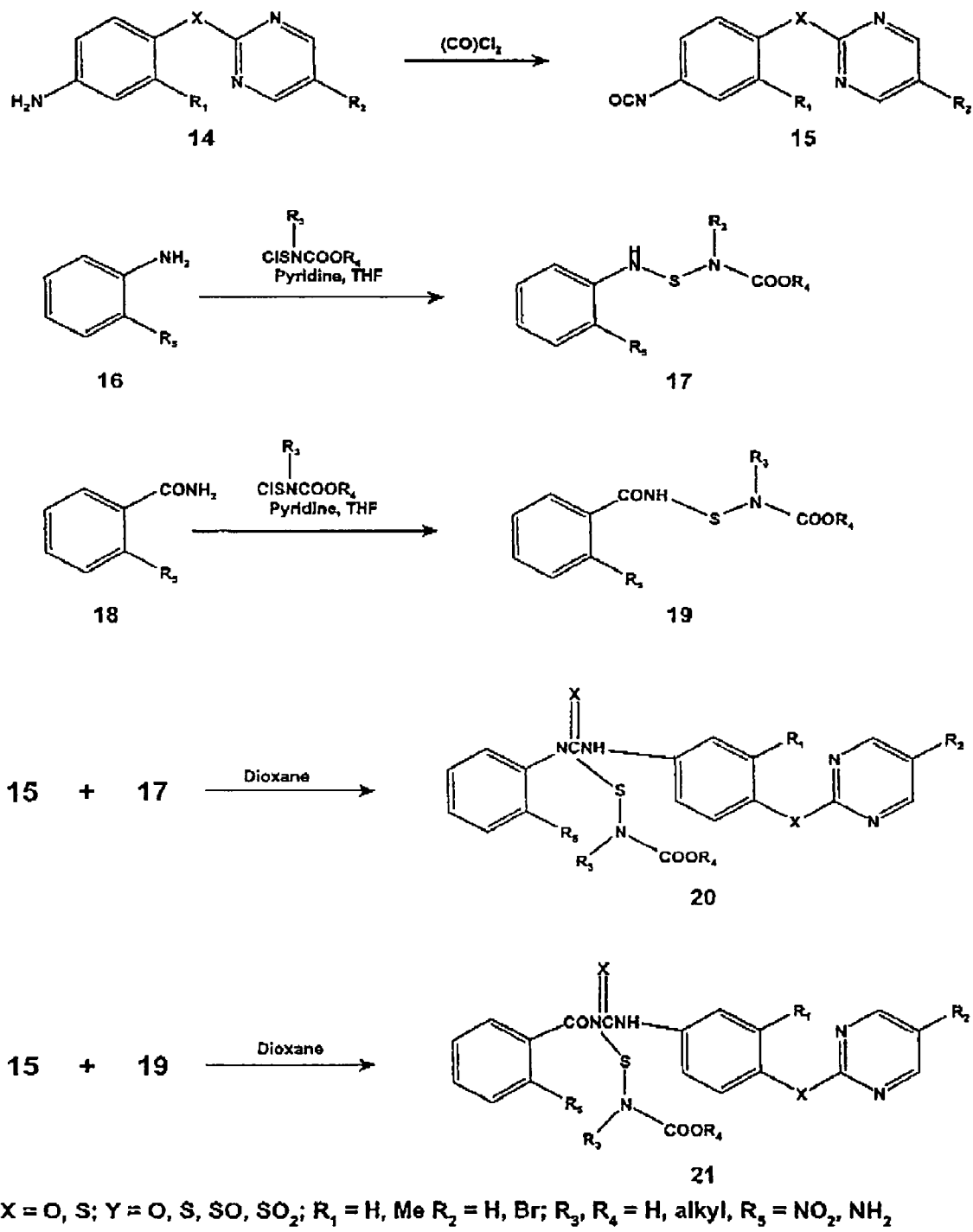

FIG. 4 schematically depicts the synthesis scheme for compounds 4a and 4b of the present invention.

Figure 5:
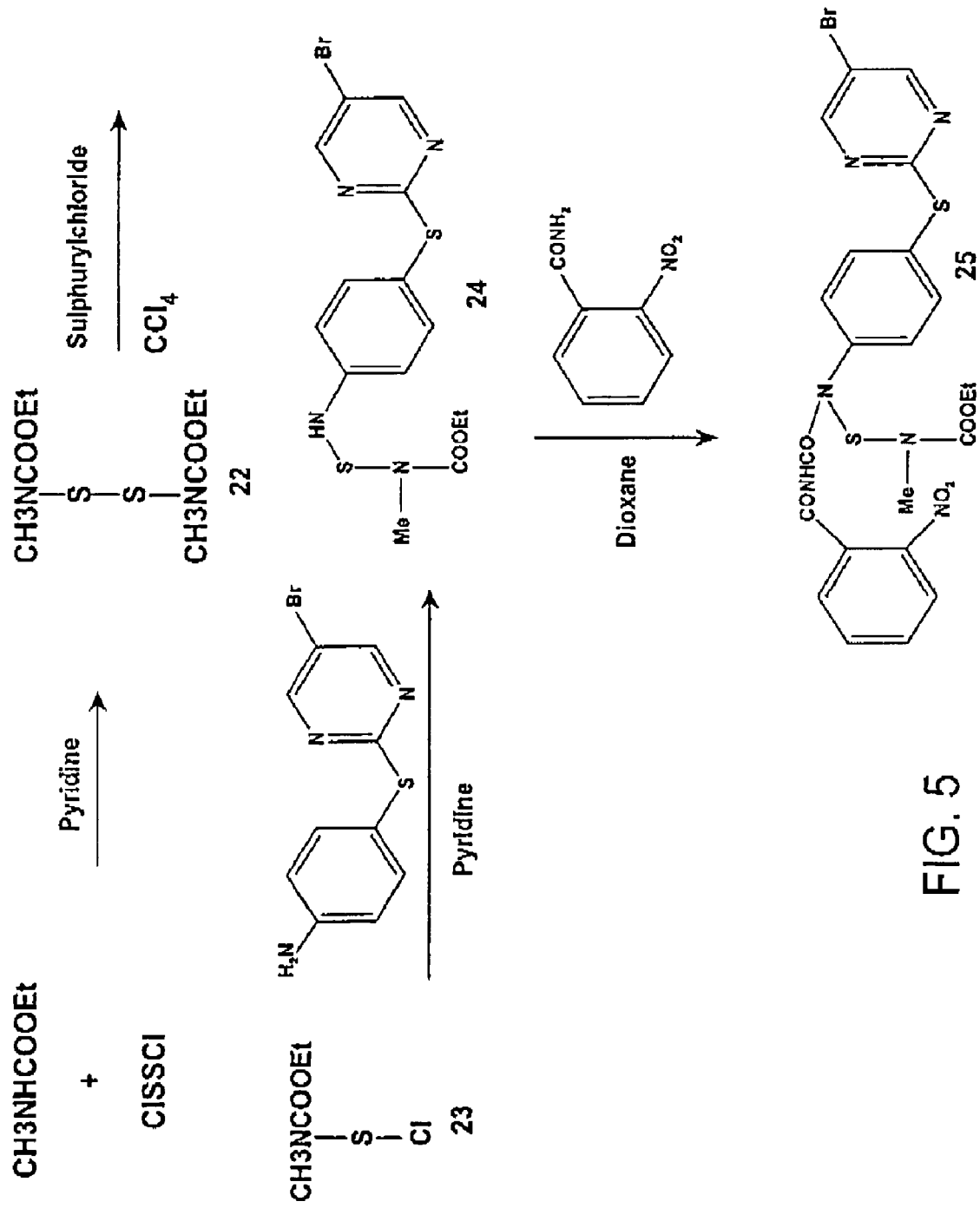

FIG. 5 schematically depicts the synthesis scheme for compounds of the present invention.

Figure 6:
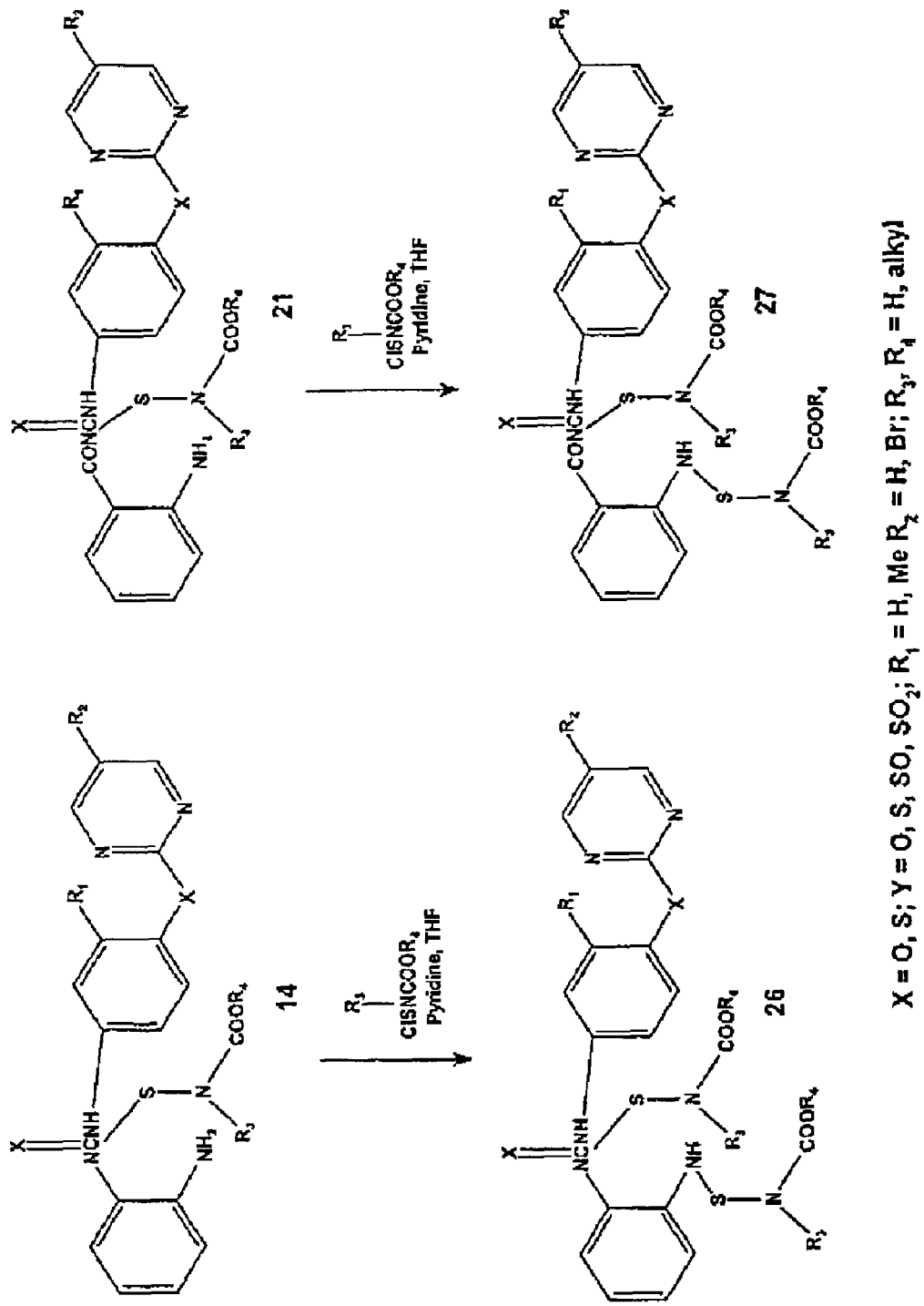

FIG. 6 schematically depicts the synthesis scheme for both ring-a and urea modified prodrugs of the present invention.

Figure 7:
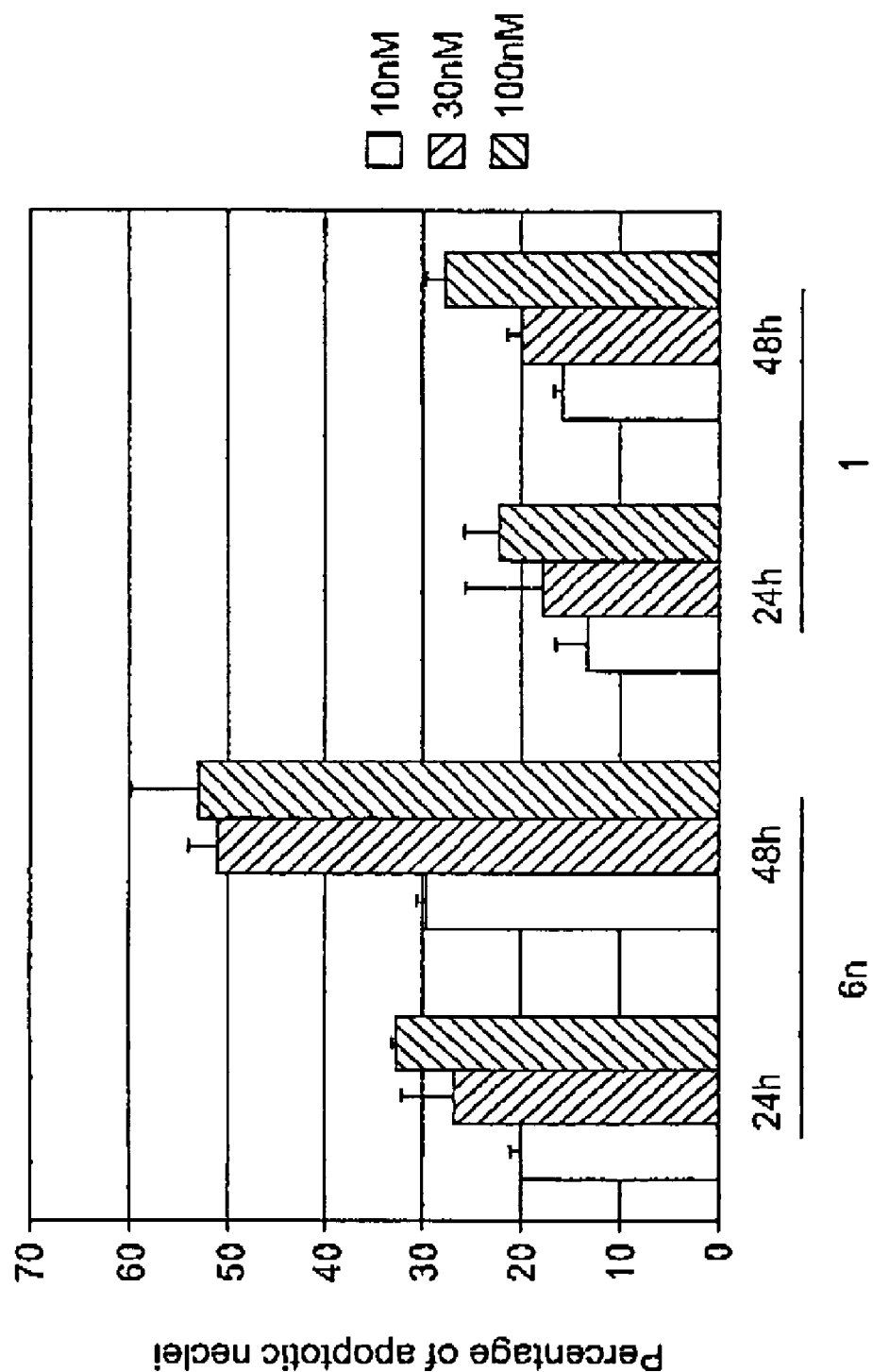

FIG. 7 is a bar graph demonstrating the apoptosis of MCF-7 cells by compounds 6n and 1.

Figure 8:
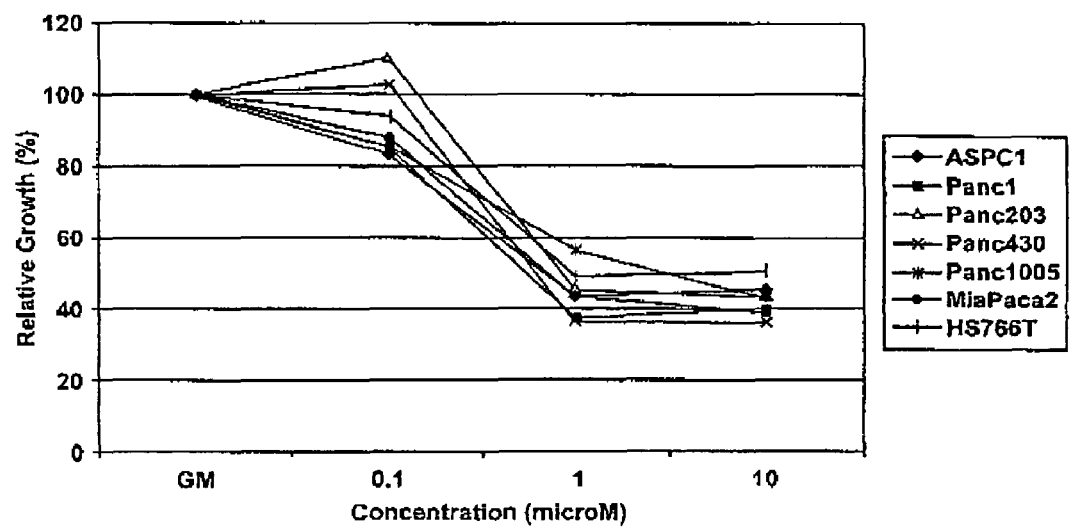

FIG. 8 depicts the dose response curves generated by exposing seven pancreatic cell lines to various concentrations of compound 1 as a control.

Figure 9:
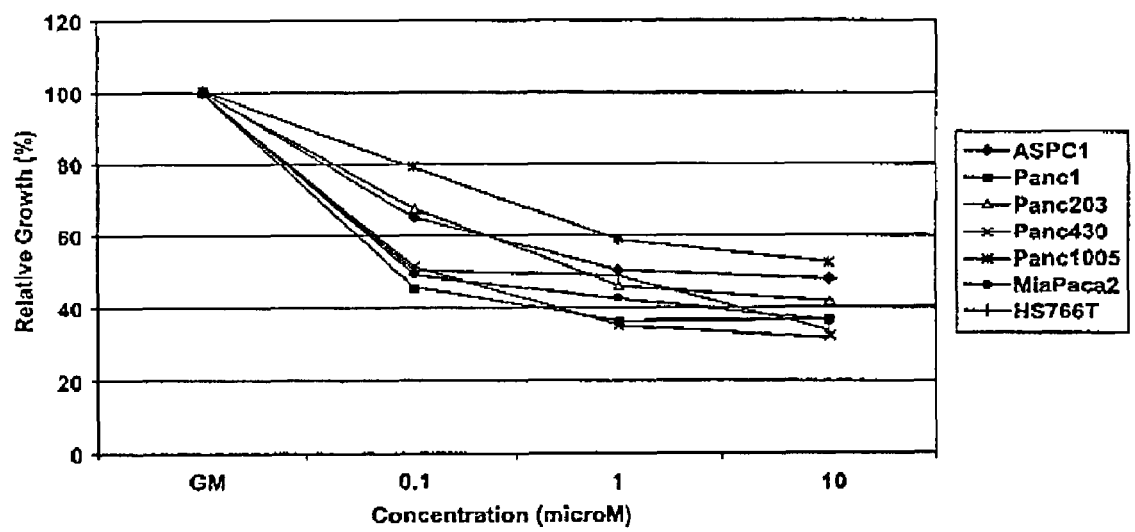

FIG. 9 depicts the dose response curves generated by exposing seven pancreatic cell lines to various concentrations of compound 6n of the present invention.

Figure 10:
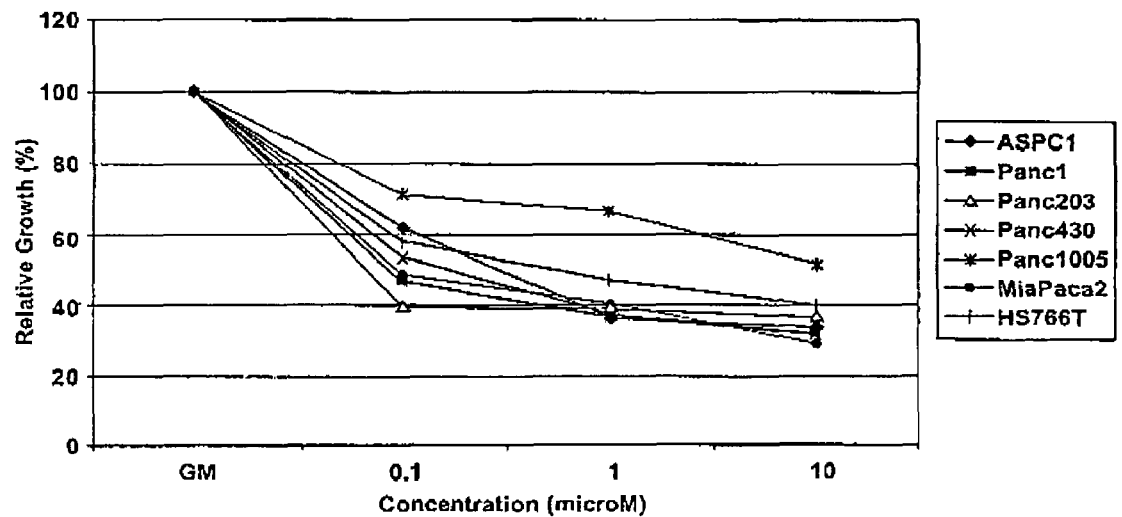

FIG. 10 depicts the dose response curves generated by exposing seven pancreatic cell lines to various concentrations of compound 7d of the present invention.

Figure 11:
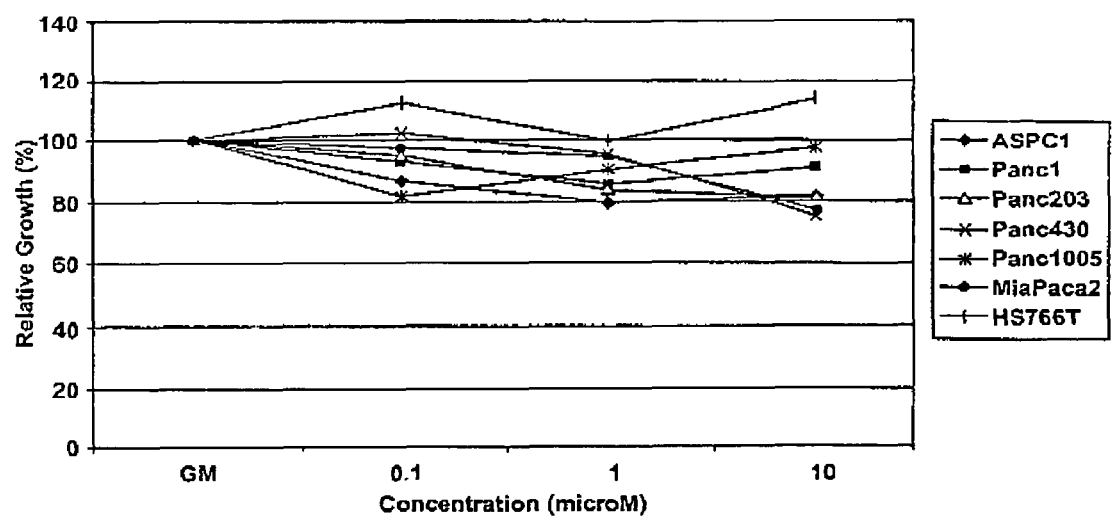

FIG. 11 depicts the dose response curves generated by exposing seven pancreatic cell lines to various concentrations of compound 6d of the present invention.

Figure 12:
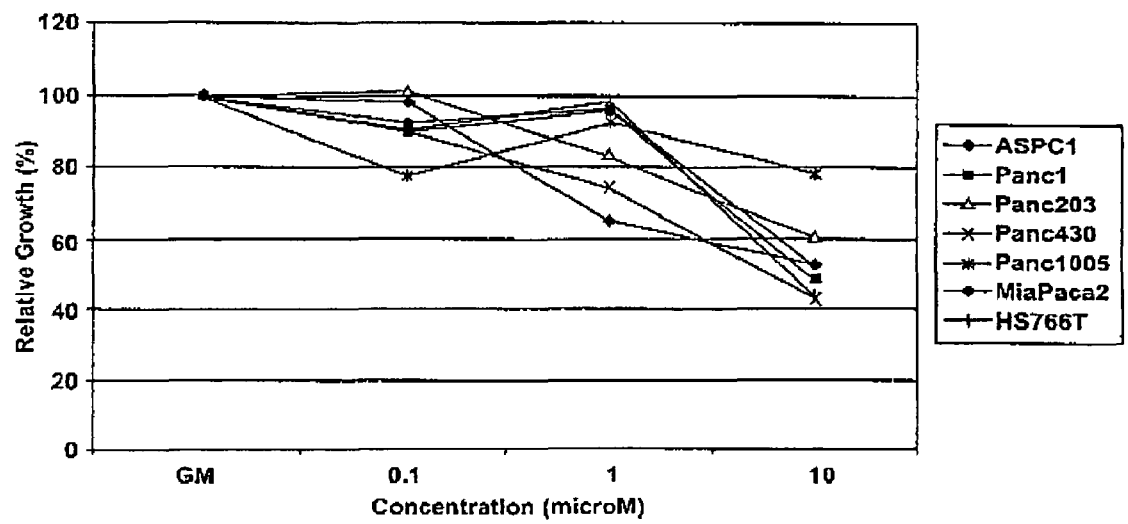

FIG. 12 depicts the dose response curves generated by exposing seven pancreatic cell lines to various concentrations of compound 6h of the present invention.

Figure 13:
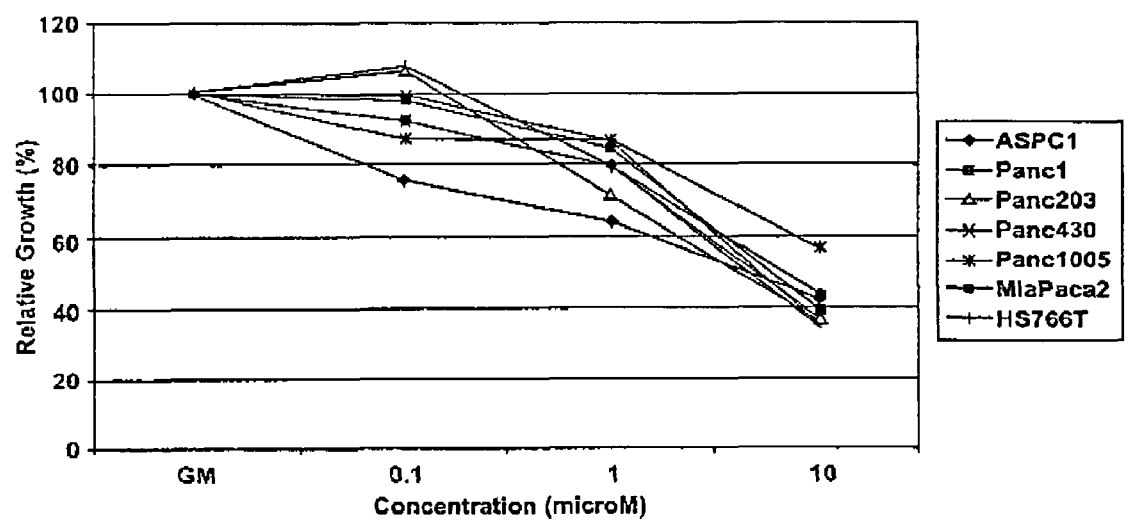

FIG. 13 depicts the dose response curves generated by exposing seven pancreatic cell lines to various concentrations of compound 7b of the present invention.

Figure 14:
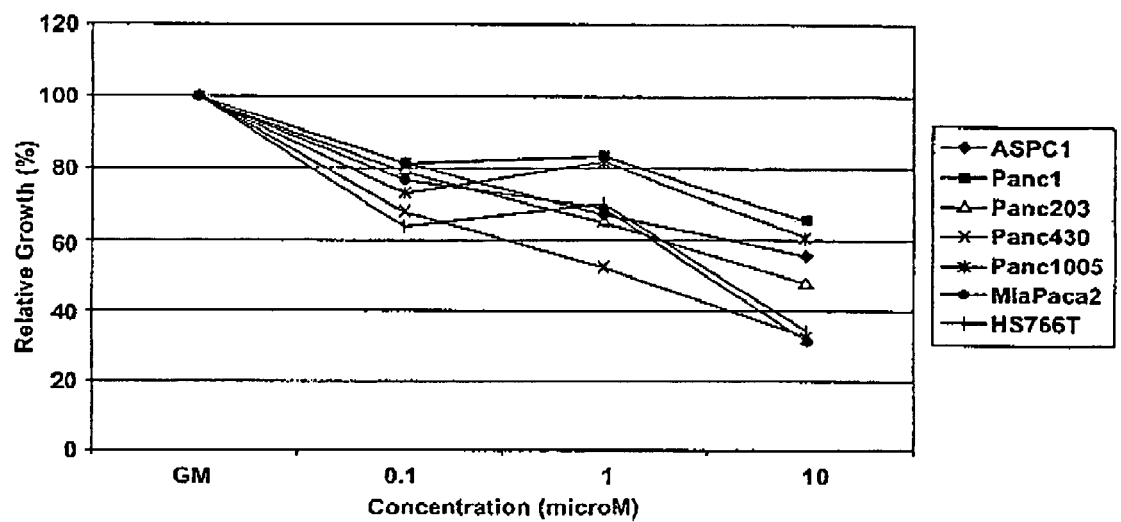

FIG. 14 depicts the dose response curves generated by exposing seven pancreatic cell lines to various concentrations of compound 6g of the present invention.

Figure 15:
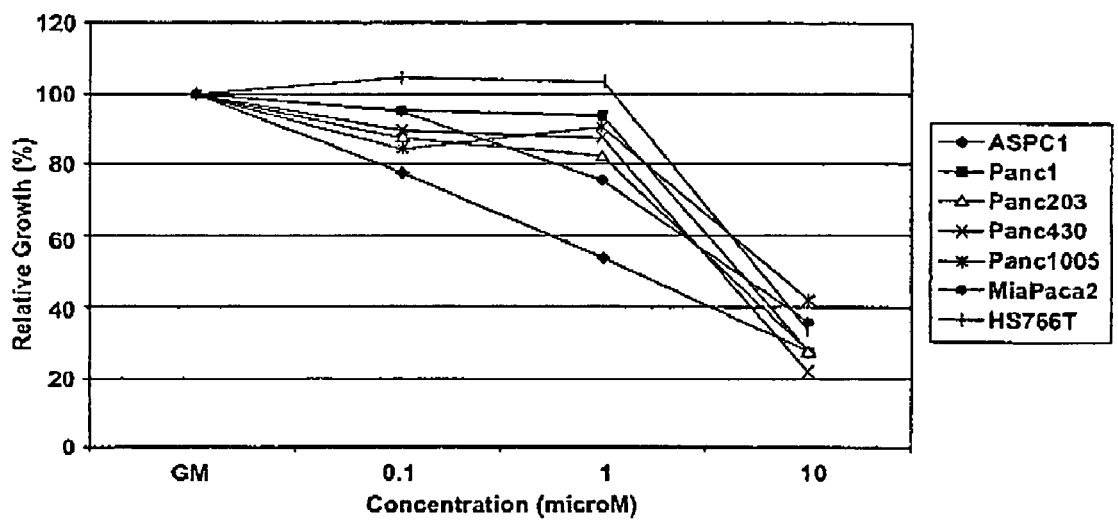

FIG. 15 depicts the dose response curves generated by exposing seven pancreatic cell lines to various concentrations of compound 8g of the present invention.

Figure 16:
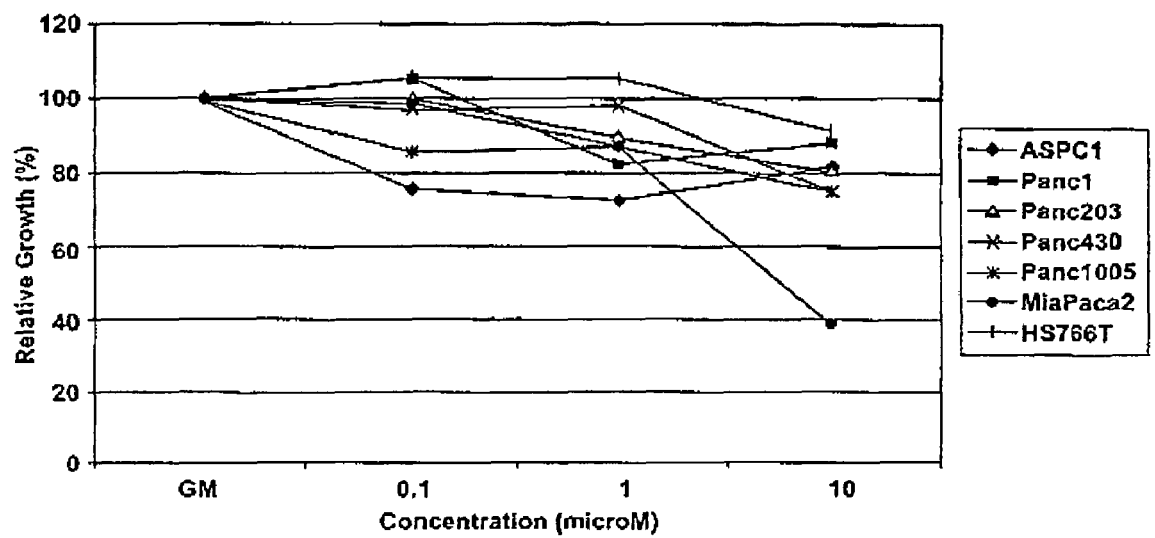

FIG. 16 depicts the dose response curves generated by exposing seven pancreatic cell lines to various concentrations of compound 8h of the present invention.

Figure 17:
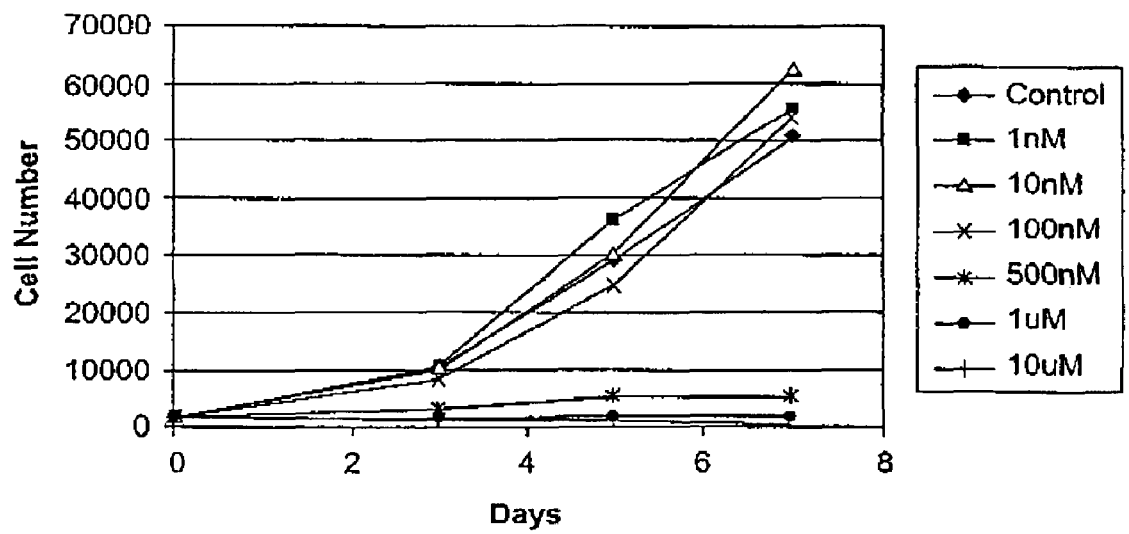

FIG. 17 depicts the dose response curves generated by exposing various concentrations of compound 1 of the present invention to human prostate cancer cell line LAPC-4 versus a control using only a solvent.

Figure 18:
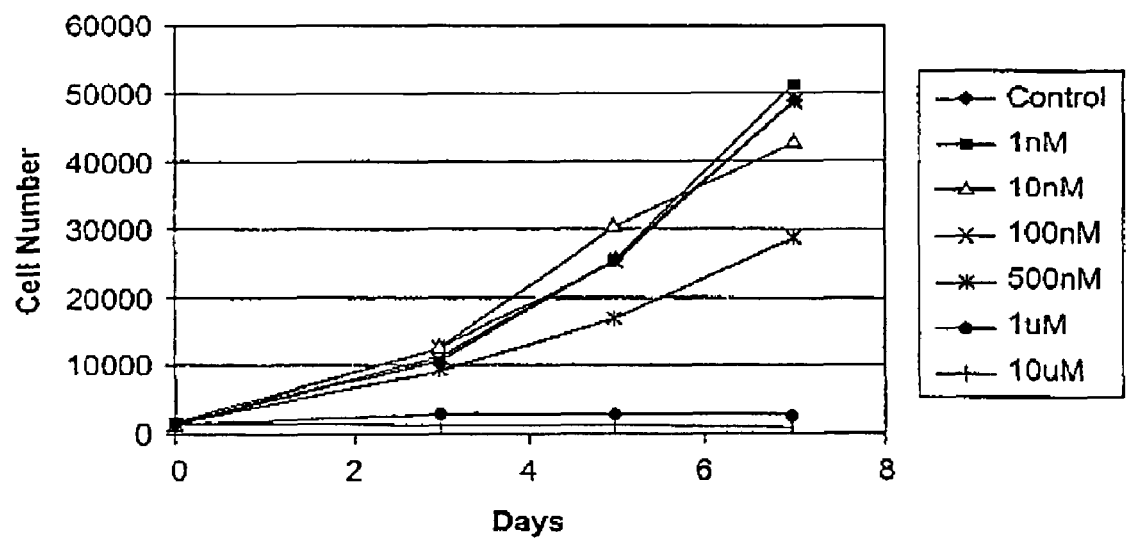

FIG. 18 depicts the dose response curves generated by exposing various concentrations of compound 6l of the present invention to human prostate cancer cell line LAPC-4 versus a control using only a solvent.

Figure 19:
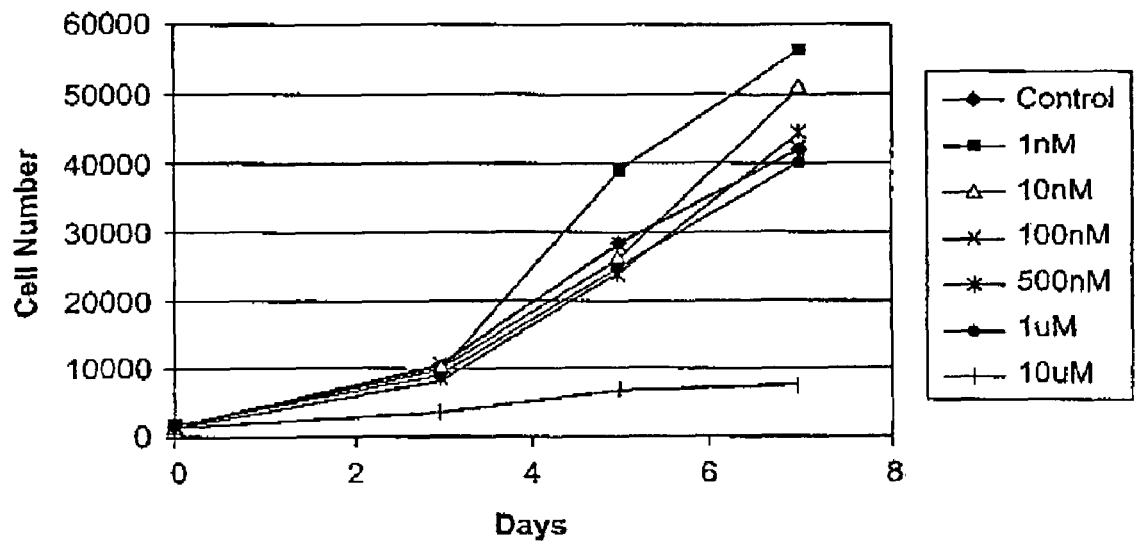

FIG. 19 depicts the dose response curves generated by exposing various concentrations of compound 6h of the present invention to human prostate cancer cell line LAPC-4 versus a control using only a solvent.

Figure 20:
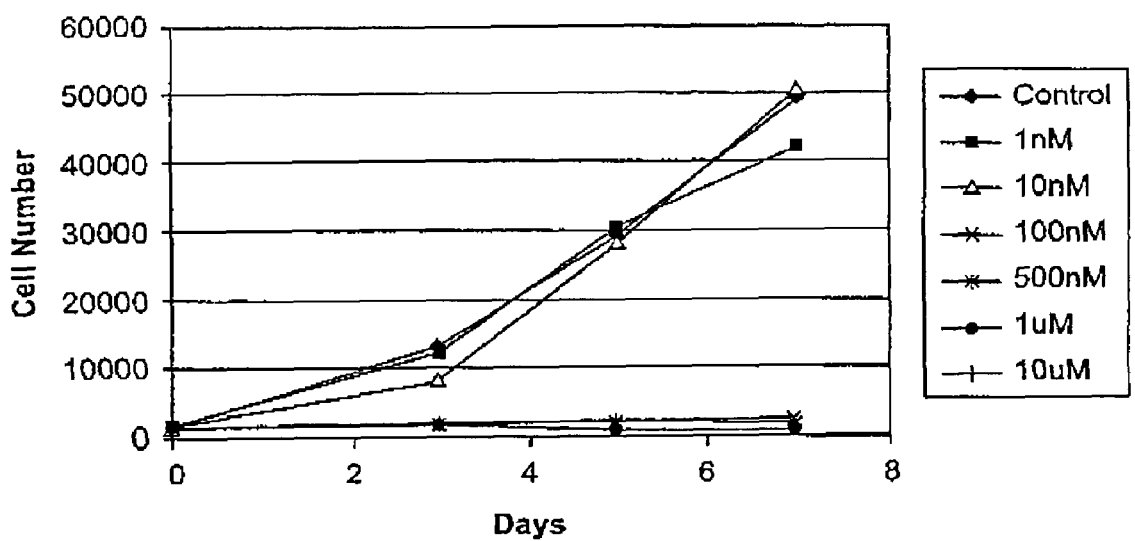

FIG. 20 depicts the dose response curves generated by exposing various concentrations of compound 6n of the present invention to human prostate cancer cell line LAPC-4 versus a control using only a solvent.

Figure 21:
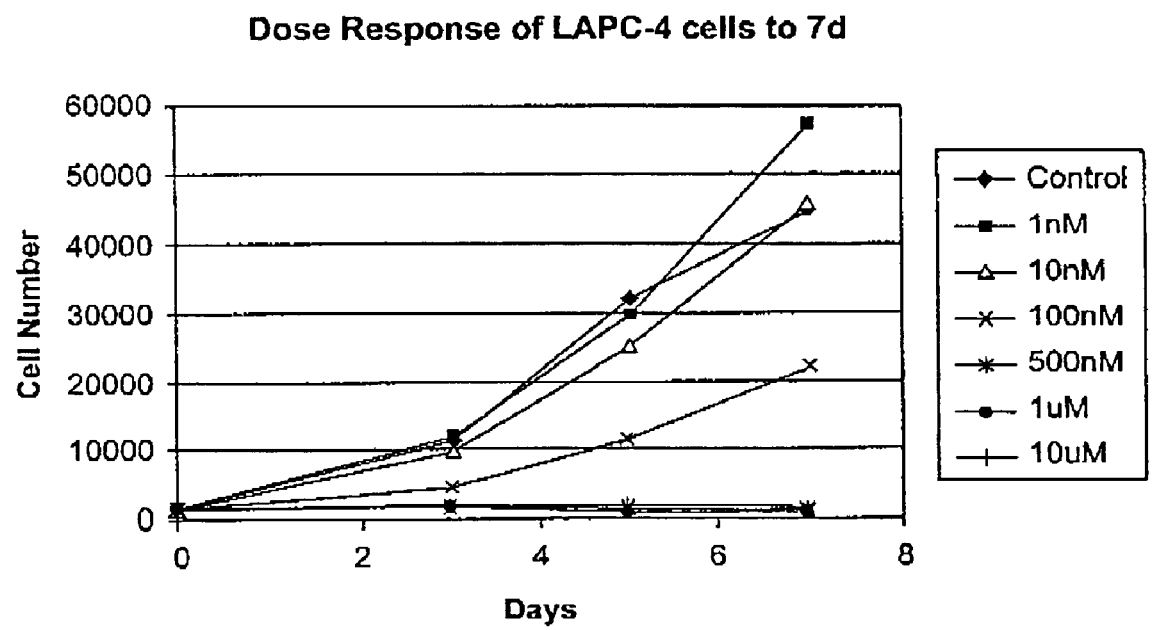

FIG. 21 depicts the dose response curves generated by exposing various concentrations of compound 7d of the present invention to human prostate cancer cell line LAPC-4 versus a control using only a solvent.

Figure 22:
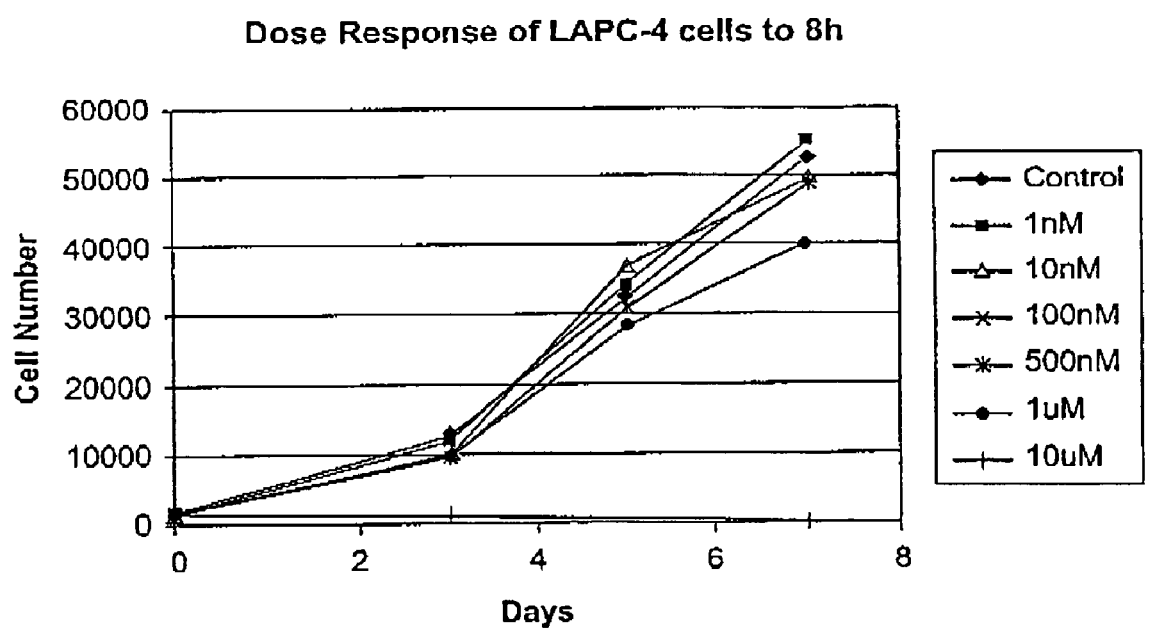

FIG. 22 depicts the dose response curves generated by exposing various concentrations of compound 8h of the present invention to human prostate cancer cell line LAPC-4 versus a control using only a solvent.

Figure 23:
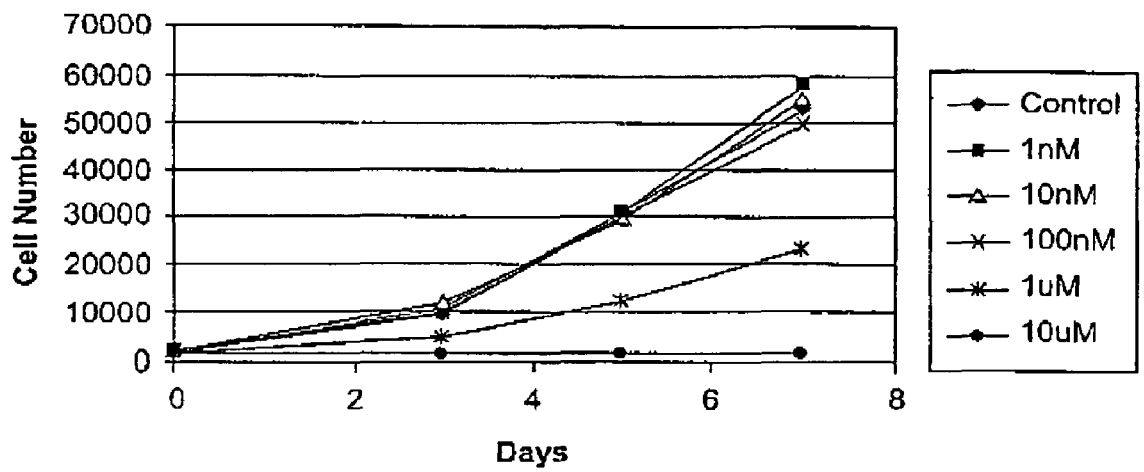

FIG. 23 depicts the dose response curves generated by exposing various concentrations of compound 1 of the present invention to human prostate cancer cell line CWR22R versus a control using only a solvent.

Figure 24:
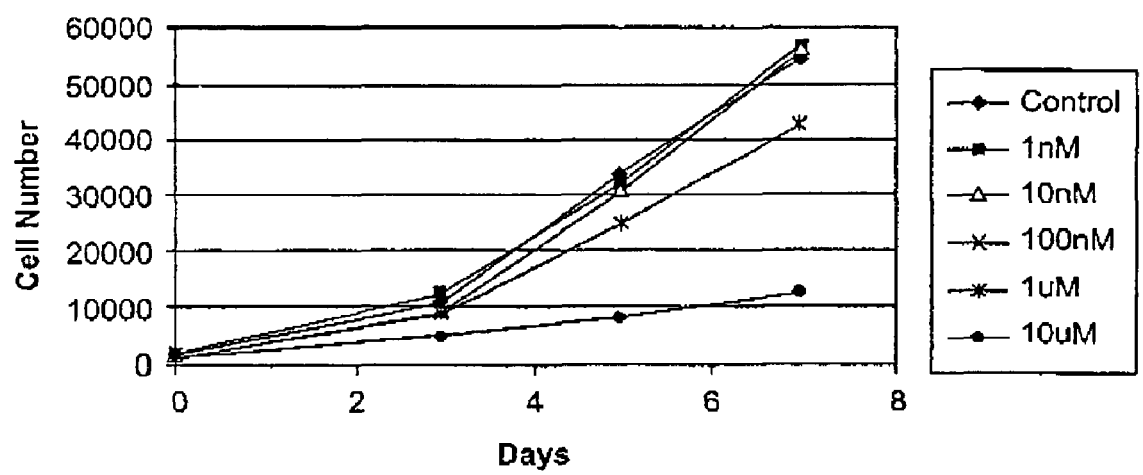

FIG. 24 depicts the dose response curves generated by exposing various concentrations of compound 6l of the present invention to human prostate cancer cell line CWR22R versus a control using only a solvent.

Figure 25:
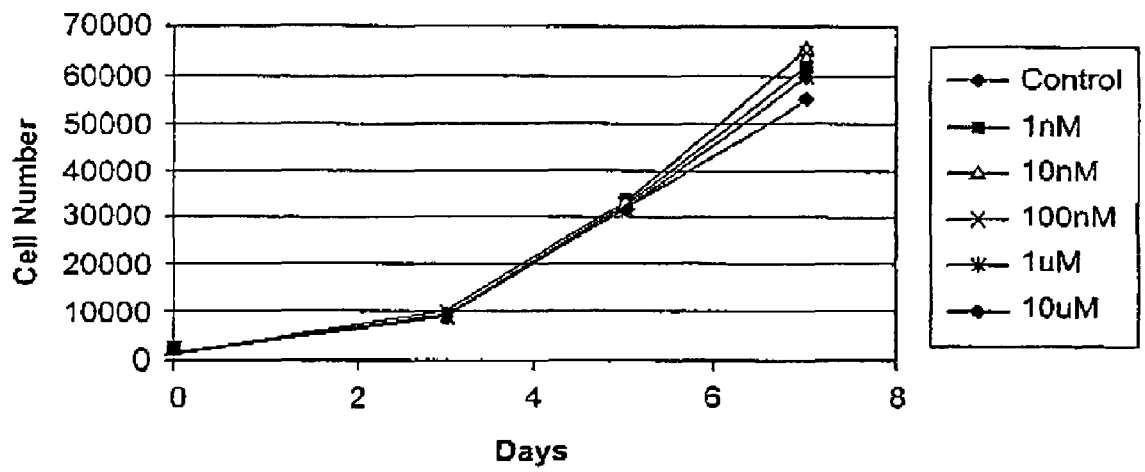

FIG. 25 depicts the dose response curves generated by exposing various concentrations of compound 6h of the present invention to human prostate cancer cell line CWR22R versus a control using only a solvent.

Figure 26:
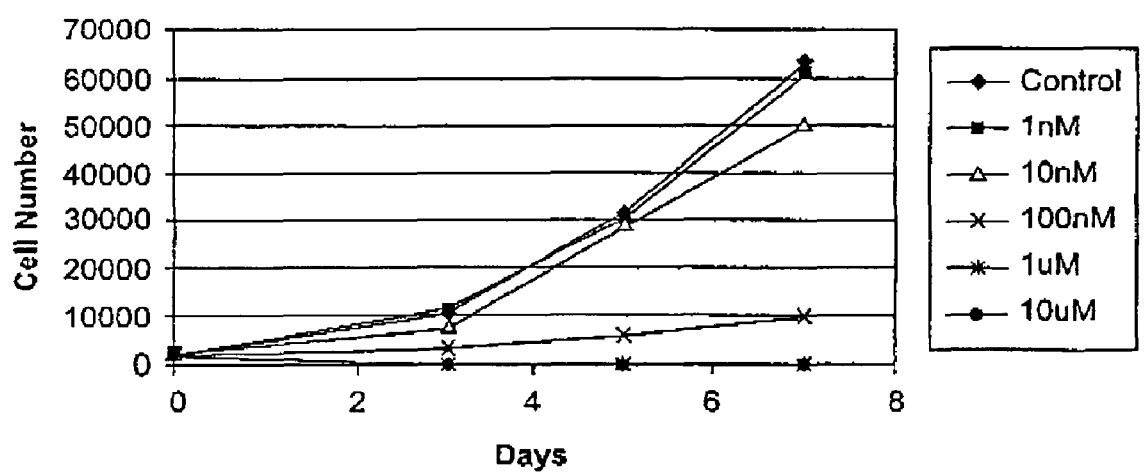

FIG. 26 depicts the dose response curves generated by exposing various concentrations of compound 6n of the present invention to human prostate cancer cell line CWR22R versus a control using only a solvent.

Figure 27:
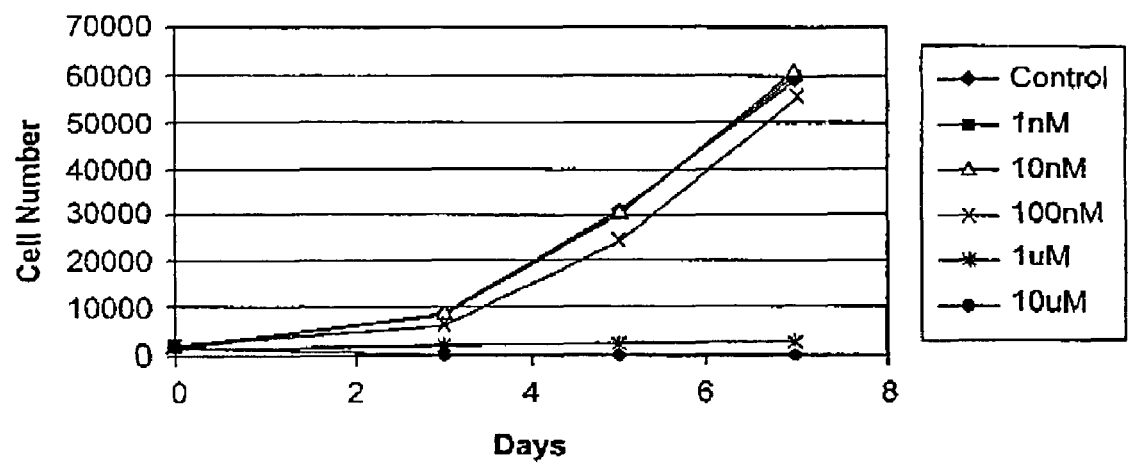

FIG. 27 depicts the dose response curves generated by exposing various concentrations of compound 7d of the present invention to human prostate cancer cell line CWR22R versus a control using only a solvent.

Figure 28:
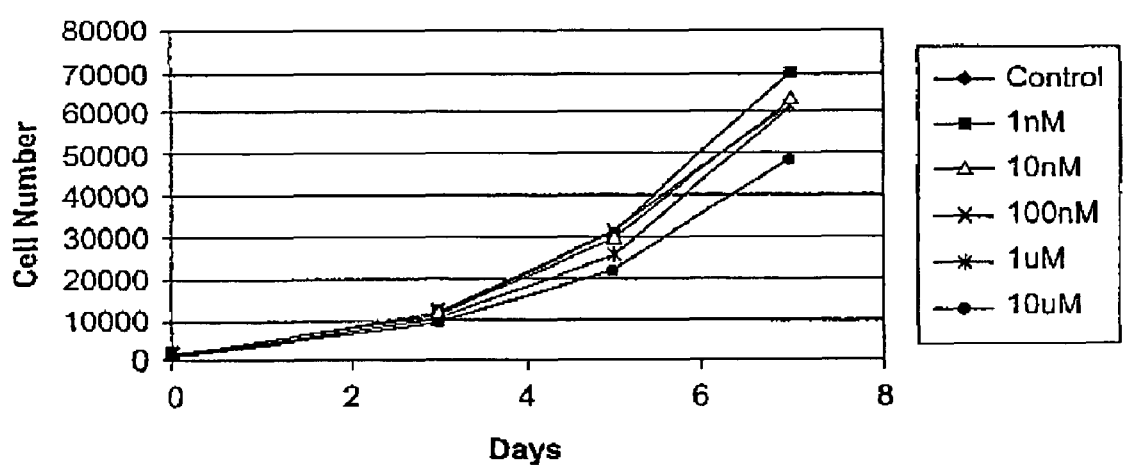

FIG. 28 depicts the dose response curves generated by exposing various concentrations of compound 8h of the present invention to human prostate cancer cell line CWR22R versus a control using only a solvent.

Figure 29:
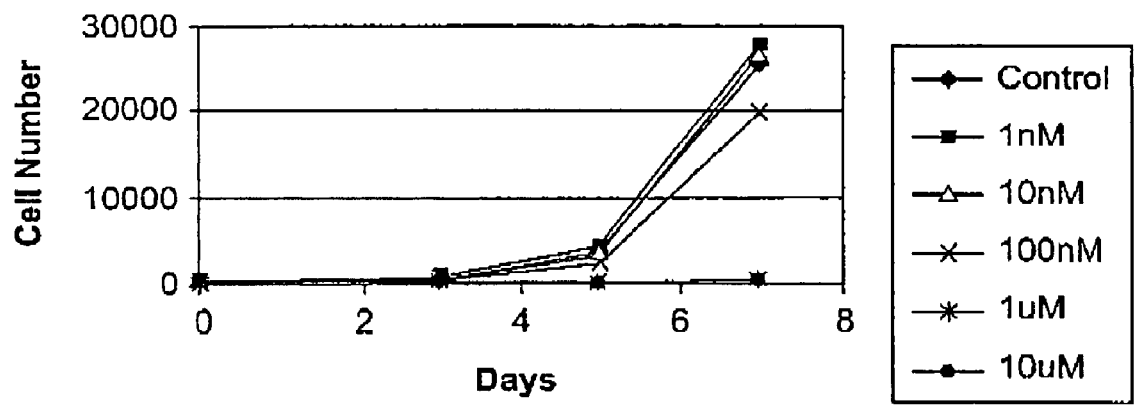

FIG. 29 depicts the dose response curves generated by exposing various concentrations of compound 1 of the present invention to human prostate cancer cell line LnCaP versus a control using only a solvent.

Figure 30:
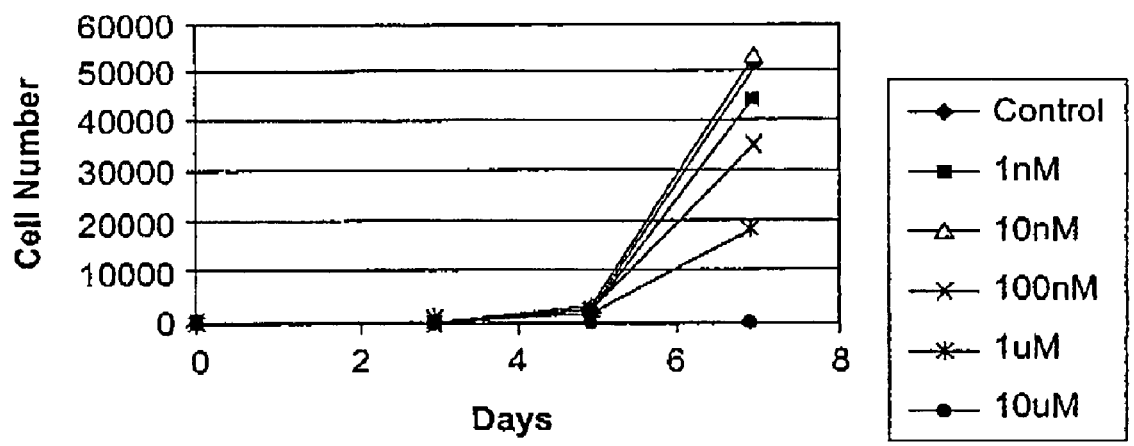

FIG. 30 depicts the dose response curves generated by exposing various concentrations of compound 6l of the present invention to human prostate cancer cell line LnCaP versus a control using only a solvent.

Figure 31:
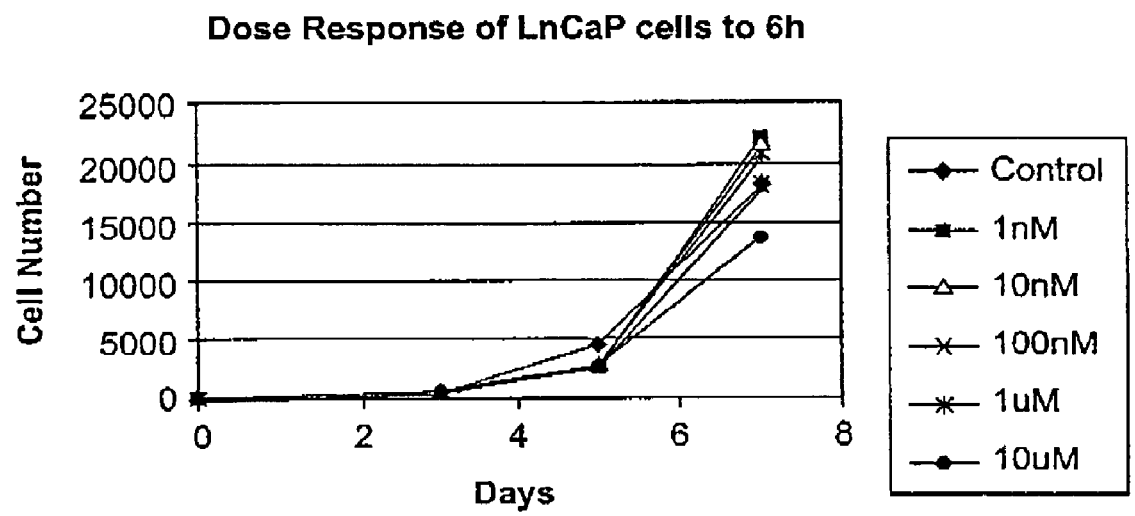

FIG. 31 depicts the dose response curves generated by exposing various concentrations of compound 6h of the present invention to human prostate cancer cell line LnCaP versus a control using only a solvent.

Figure 32:
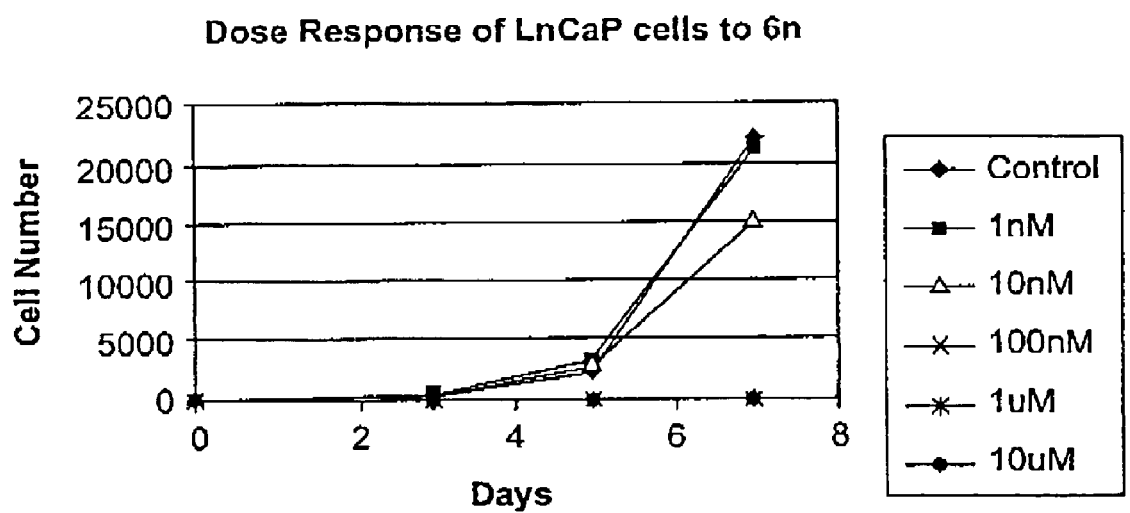

FIG. 32 depicts the dose response curves generated by exposing various concentrations of compound 6n of the present invention to human prostate cancer cell line LnCaP versus a control using only a solvent.

Figure 33:
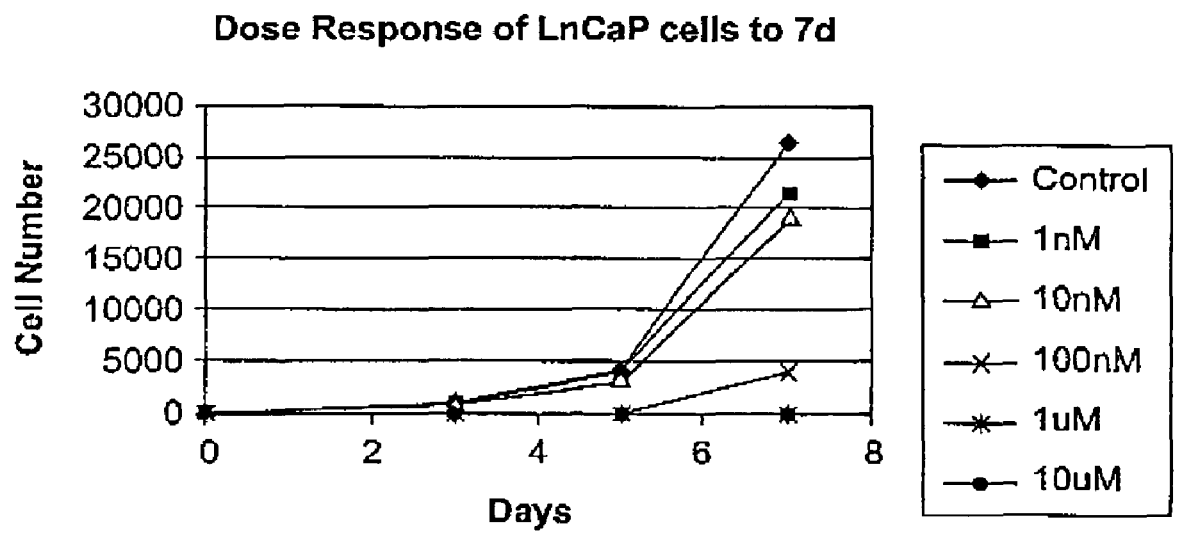

FIG. 33 depicts the dose response curves generated by exposing various concentrations of compound 7d of the present invention to human prostate cancer cell line LnCaP versus a control using only a solvent.

Figure 34:
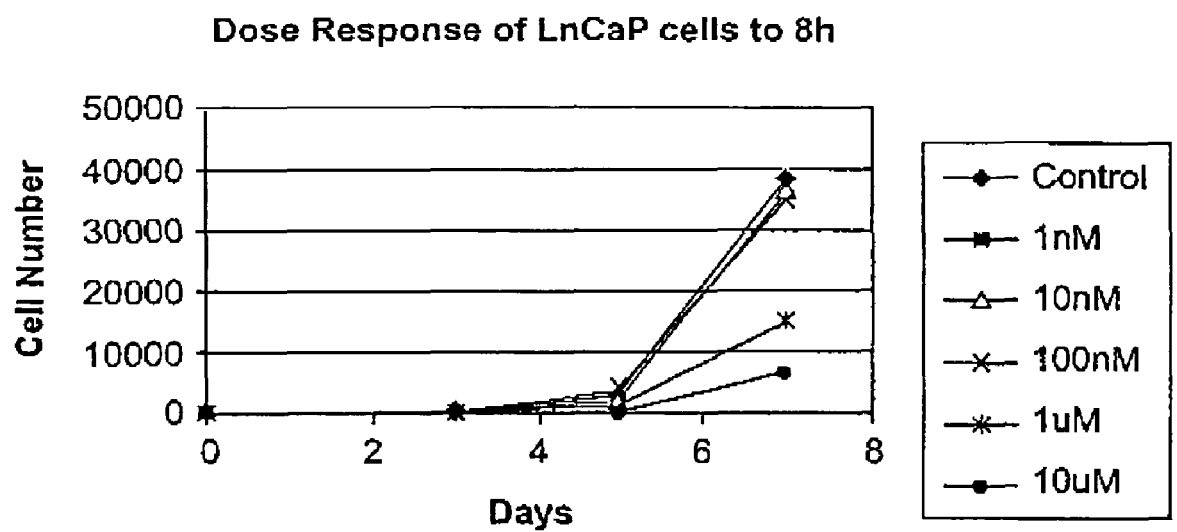

FIG. 34 depicts the dose response curves generated by exposing various concentrations of compound 8h of the present invention to human prostate cancer cell line LnCaP versus a control using only a solvent.

DETAILED DESCRIPTION OF THE INVENTION

Abbreviations and Definitions

The abbreviations used herein have their conventional meaning within the chemical and biological arts.

Where moieties are specified by their conventional chemical formulae, written from left to right, they equally encompass the chemically identical moieties that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, including those groups having 10 or fewer carbon atoms. A "lower alkyl" or "lower alkylene" is a shorter chain alkyl or alkylene group, generally having eight or fewer carbon atoms.

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and a heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituent moieties for each of the above noted aryl and heteroaryl ring systems may be selected from the group of acceptable substituent moieties described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituent moieties for each type of radical are provided below.

Substituent moieties for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', —halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituent moieties, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituent moieties described for the alkyl radical, substituent moieties for the aryl and heteroaryl groups are varied and may be selected from, for example: halogen, —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituent moieties on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituent moieties on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituent moieties on adjacent atoms of the aryl or heteroaryl ring may optionally be replaced with a substituent of the formula —(CRR')$_s$—X'—(C"R''')$_d$-, where s and d are independently integers of from 0 to 3, and X' is —O—, —NR'—, —S—, —S(O)—, —S(O)$_2$—, or —S(O)$_2$NR'—. The substituent moieties R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The term "pharmaceutically acceptable salts" is meant to include salts of the active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Where two groups are "optionally joined together to form a ring," the two groups are covalently bonded together with the atom or atoms to which the two groups are joined to form a substituted or unsubstituted aryl, a substituted or unsubstituted heteroaryl, a substituted or unsubstituted cycloalkyl, or a substituted or unsubstituted heterocycloalkyl ring.

The terms "arylalkyl," "heteroarylalkyl," "cycloalkyl-alkyl," and "heterocycloalkyl-alkyl," as used herein, refer to an aryl, heteroaryl, cycloalkyl and heterocycloalkyl, respectively, attached to the remainder of the molecule via an alkylene group. Where an "arylalkyl," "heteroarylalkyl," "cycloalkyl-alkyl," or "heterocycloalkyl-alkyl" is substituted, one or more substituent moieties may be covalently bonded to the alkylene moiety and/or the aryl, heteroaryl, cycloalkyl and heterocycloalkyl moieties, respectively. A "$C_1$-$C_{20}$" arylalkyl, heteroarylalkyl, cycloalkyl-alkyl, or heterocycloalkyl-alkyl, are moieties in which a $C_1$-$C_{20}$ alkylene links an aryl, heteroaryl, $C_4$-$C_8$ cycloalkyl, and 4 to 8 membered heterocycloalkyl, respectively, to the remainder of the molecule. A "$C_1$-$C_8$" arylalkyl, heteroarylalkyl, cycloalkyl-alkyl, or heterocycloalkyl-alkyl, are moieties in which a $C_1$-$C_8$ alkylene links an aryl, heteroaryl, $C_5$-$C_7$ cycloalkyl, and 5 to 7 membered heterocycloalkyl, respectively, to the remainder of the molecule A "substituent group," as used herein, means a group selected from the following moieties:
(A) —OH, —$NH_2$, —SH, —CN, —$CF_3$, oxy, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
 (i) oxy, —OH, —$NH_2$, —SH, —CN, —$CF_3$, halogen, unsubstituted alkyl, unsubstituted heteroalkyl, unsubstituted cycloalkyl, unsubstituted heterocycloalkyl, unsubstituted aryl, unsubstituted heteroaryl, and
 (ii) alkyl, heteroalkyl, cycloalkyl, heterocycloalkyl, aryl, and heteroaryl, substituted with at least one substituent selected from:
  (a) oxy, —OH, —$NH_2$, —SH, —CN, —$CF_3$, halogen, unsubstituted alkyl, unsubstituted heteroalkyl, unsubstituted cycloalkyl, unsubstituted heterocycloalkyl, unsubstituted aryl, unsubstituted heteroaryl, and
  (b) alkyl, heteroalkyl, cycloalkyl, heterocycloalkyl, aryl, or heteroaryl, substituted with at least one substituent selected from oxy, —OH, —$NH_2$, —SH, —CN, —$CF_3$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the methods of the invention successfully treat a patient's delirium by decreasing the incidence of disturbances in consciousness or cognition.

The term "higher alkyl" refers to those alkyl groups having at least six carbon atoms. The term "lower alkyl" refers to those alkyl groups having from one to five carbon atoms.

DESCRIPTION OF THE EMBODIMENTS

I. Compounds of the Present Invention

In one aspect, the present invention provides an antiproliferative, water soluble compound with high bioavailability having the general formula (I)

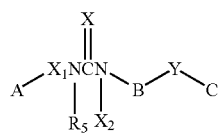
(I)

Where A, B, and C are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur; 'Y' is sulfur, sulfoxide or sulfone; $X_1$ is CO or hydrogen; $R_5$ is hydrogen, or alkyl or aryl group; $X_2$ is hydrogen or $SR_6$, wherein $R_6$ is a substituted alkyl, cycloalkyl, aryl, heterocycle, or substituted phenyl fused with a saturated or unsaturated 4-to 6-membered rings optionally containing one to three heteroatoms independently selected from N, O, and S.

The present invention is further defined by compounds having the general formulas (II)-(XIX):

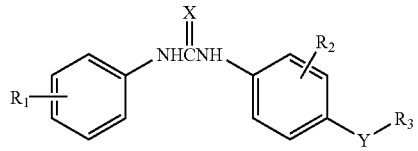
(II)

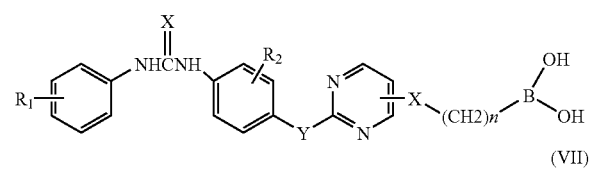
(III)

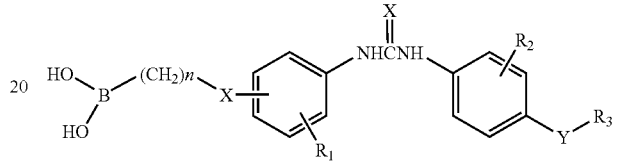
(IV)

Where $R_1$, $R_3$ is H, F, Cl, Br, I, CN, $NO_2$, $NH_2$, NHMe, $NMe_2$, $CF_3$, COOH, CONHOH, alkyl or aryl, group; $R_5$ is alkyl or aryl group; $R_4$ is substituted pyridine, pyrimidine, thiazole, pyrrazole, benzothiozole, indole, benzofuran or any heterocyclic ring; 'X' is oxygen or sulfur; 'Y' is sulfur, sulfoxide or sulfone; n is any integer.

(V)

(VI)

(VII)

Where $R_1$, $R_2$ is H, F, Cl, Br, I, CN, $NO_2$, $NH_2$, NHMe, NMe2, $CF_3$, COOH, CONHOH, alkyl or aryl, group; $R_3$ is substituted pyridine, pyrimidine, thiazole, pyrrazole, benzothiozole, indole, benzofuran or any heterocyclic ring; 'X' is oxygen or sulfur; 'Y' is sulfur, sulfoxide or sulfone; n is any integer.

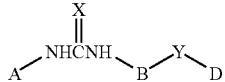
(VIII)

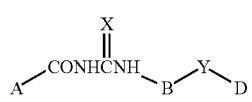
(IX)

Where A, B, and D are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur; 'Y' is sulfur, sulfoxide or sulfone.

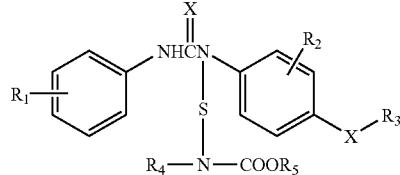
(XII)

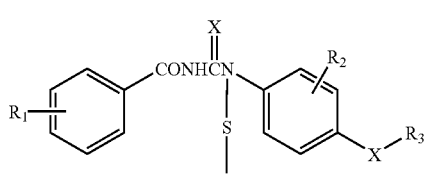
(XIII)

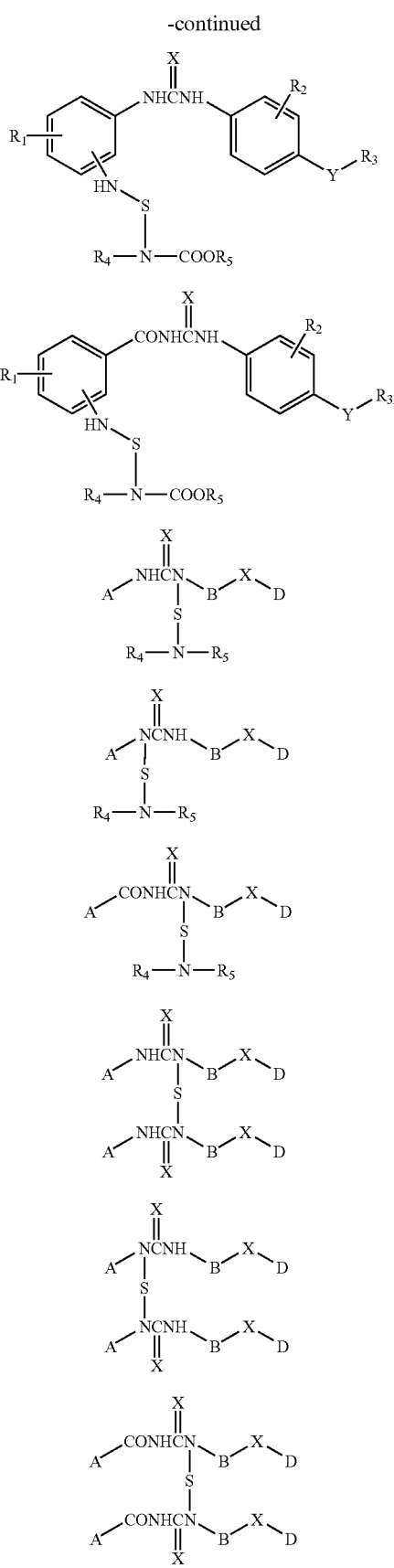

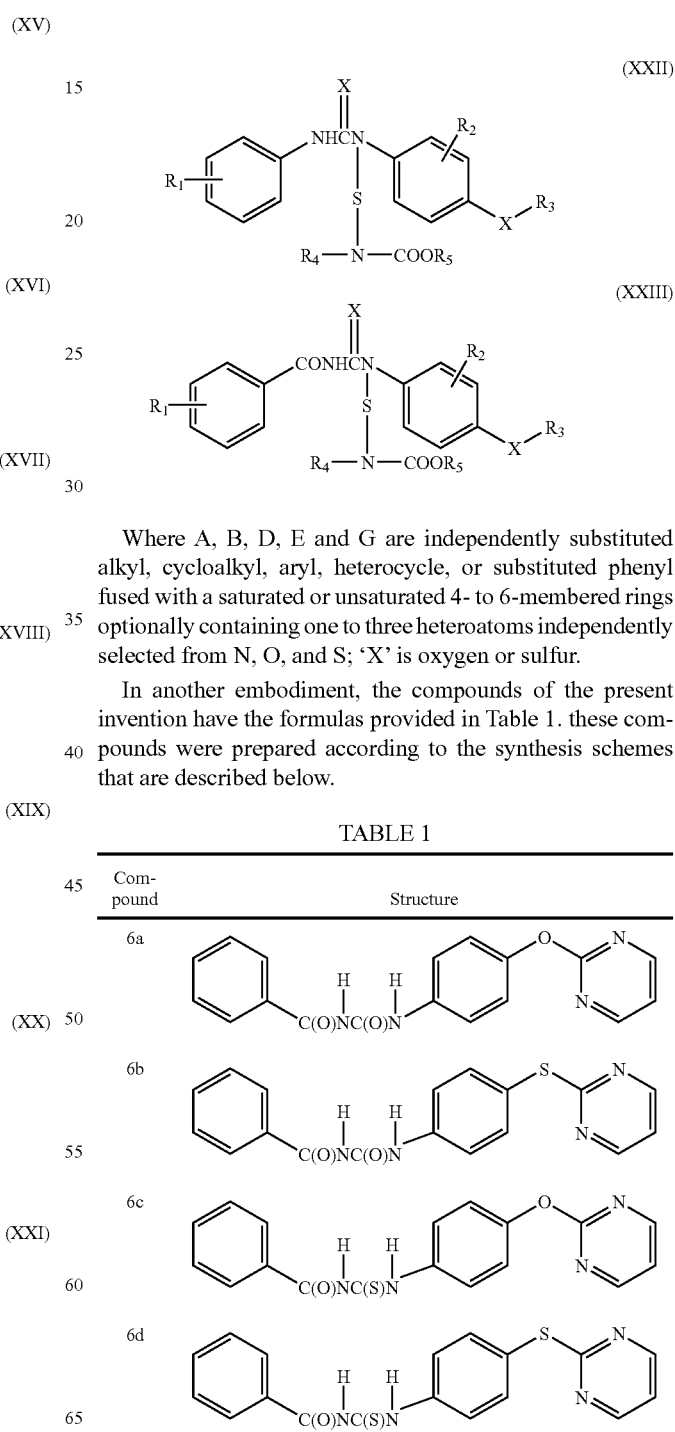

Where $R_1$, $R_2$ is H, F, Cl, Br, I, CN, $NO_2$, $NH_2$, NHMe, $NMe_2$, $CF_3$, COOH, CONHOH, alkyl or aryl, group; $R_3$ is substituted pyridine, pyrimidine, thiazole, pyrrazole, benzothiozole, indole, benzofuran or any heterocyclic ring; $R_4$, $R_5$ is substituted alkyl or aryl group; 'X' is oxygen or sulfur.

Where A, B, D, E and F are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur.

Where A, B, D, E and G are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur.

In another embodiment, the compounds of the present invention have the formulas provided in Table 1. these compounds were prepared according to the synthesis schemes that are described below.

TABLE 1-continued

| Compound | Structure |
|---|---|
| 6e | Ph-C(O)N(H)C(O)N(H)-C6H4-O-pyrimidine-Br |
| 6f | Ph-C(O)N(H)C(S)N(H)-C6H4-O-pyrimidine-Br |
| 6g | Ph-C(O)N(H)C(O)N(H)-C6H4-S-pyrimidine-Br |
| 6h | Ph-C(O)N(H)C(S)N(H)-C6H4-S-pyrimidine-Br |
| 6i | Ph-C(O)N(H)C(O)N(H)-C6H3(Me)-O-pyrimidine-Br |
| 6j | Ph-C(O)N(H)C(S)N(H)-C6H3(Me)-O-pyrimidine-Br |
| 6k | (2-NO2)C6H4-C(O)N(H)C(O)N(H)-C6H4-O-pyrimidine |
| 6l | (2-NO2)C6H4-C(O)N(H)C(O)N(H)-C6H4-S-pyrimidine |
| 6m | (2-NO2)C6H4-C(O)N(H)C(O)N(H)-C6H4-O-pyrimidine-Br |
| 6n | (2-NO2)C6H4-C(O)N(H)C(O)N(H)-C6H4-S-pyrimidine-Br |
| 7a | (2-NH2)C6H4-C(O)N(H)C(O)N(H)-C6H4-O-pyrimidine |
| 7b | (2-NH2)C6H4-C(O)N(H)C(O)N(H)-C6H4-S-pyrimidine |
| 7c | (2-NH2)C6H4-C(O)N(H)C(O)N(H)-C6H4-O-pyrimidine-Br |
| 7d | (2-NH2)C6H4-C(O)N(H)C(O)N(H)-C6H4-S-pyrimidine-Br |
| 8a | Ph-C(O)N(H)C(O)N(H)-C6H4-S(O)-pyrimidine |
| 8b | Ph-C(O)N(H)C(O)N(H)-C6H4-S(O)2-pyrimidine |
| 8c | Ph-C(O)N(H)C(O)N(H)-C6H4-S(O)-pyrimidine-Br |
| 8d | Ph-C(O)N(H)C(O)N(H)-C6H4-S(O)2-pyrimidine-Br |
| 8e | (2-NO2)C6H4-C(O)N(H)C(O)N(H)-C6H4-S(O)-pyrimidine |
| 8f | (2-NO2)C6H4-C(O)N(H)C(O)N(H)-C6H4-S(O)2-pyrimidine |
| 8g | (2-NO2)C6H4-C(O)N(H)C(O)N(H)-C6H4-S(O)-pyrimidine-Br |

TABLE 1-continued

| Compound | Structure |
|---|---|
| 8h | (structure: 2-NO2-C6H4-NH-C(O)-N-C(O)-NH-C6H4-SO2-pyrimidine-Br) |
| 9 | (structure: H2N-C6H4-S-pyrimidine-Br) |
| 10 | (structure: H2N-C6H4-S-pyrimidine) |

General Method for Synthesis of BPU Sulfur Analogs

These new analogs were synthesized in excellent yield by coupling corresponding benzoylisocyanate or benzoylisothiocyanate and aniline derivatives. Sulfur analogs of aniline intermediate were synthesized by reaction of substituted amino thiophenol with aryl halide. Sulfoxide and sulfone derivatives were prepared by oxidation of sulfides (FIG. 1). All the compounds were characterized by NMR and LC-MS studies.

Chemistry. Novel sulfur derivatives of BPU were synthesized as shown in FIG. 1. Aniline derivatives 4 were prepared by reaction of substituted aminophenols or amino thiophenols with substituted 2-chloropyrimidines in the presence of $K_2CO_3$ and DMSO.8 Condensation of substituted benzoyl isocyanates or benzoyl isothiocyanates with aniline derivatives 4 gave a series of BPU and benzoylphenylthiourea (BPTU) analogues 6a-n. Reduction of the 2-$NO_2$ group was performed using Fe and AcOH 14 to obtain the 2-$NH_2$ derivatives 7a-d. Sulfoxide and sufone derivatives 8a-h were prepared from the corresponding sulfide by oxidation with MCPBA (Heynderickx, A., et al., *Synthesis*, 1112-1116 (2003)) followed by chromatographic purification. All the compounds were characterized by spectral data analysis that confirmed the assigned structures.

Ring-A aniline modified amino acid prodrugs can prepared according to FIG. 2. The synthetic strategy involves coupling of Boc-protected amino acid with ring-A amine on the BPU compounds using coupling reagent 1-ethyl-3-(3-dimethylaminopropyl)-carbodiimide hydrochloride (WSCI.HCl). Finally Boc protection can be removed by treating with TFA. We have completed the synthesis of N,N-dimethylglycyl derivative of 7d. Other amino acid derivatives synthesis is in progress and their activity will be compared.

Ring-A aniline modifed carbamylosulfenyl derivative of BPU sulfur analog can be prepared according to FIG. 3. To prepare urea and benzoyl urea modified prodrugs, scheme 4 will be used. Compound 15 can be prepared by treating 14 with oxalyl chloride and then it can be coupled with 17 and 19 in dioxane to obtain prodrugs of general structure 20 and 21 respectively. Representative example has been shown in FIG. 5. Both ring-A and urea modified prodrugs can be prepared according to FIG. 6.

BPU compounds have very low solubility in water and limited solubility in common organic solvents. Therefore, the modification of these compounds to improve their bioavailability is expected to lead to compounds with better biological properties.

The lead prodrugs from the in vitro and in vivo studies will be then subjected to pharmacokinetic analysis to study stability, clearance and metabolism profiles.

II. Assays

Cytotoxic Evaluation of BPU Sulfur Analogs

Eight of these analogs 6d, 6h, 6n, 6g, 7b, 7d, 8g, and 8h were tested for their cytotoxicity in seven pancreatic cell lines ASPC1, Panc1, Panc203, Panc430, Pane 1005, MiaPaca2, and HS766T using MTT assay. Cells were trypsinized, seeded at 5×103 cells/well in 96-well plate and allowed to grow for 24 hours before the treatment with exponential increasing concentrations of drugs in the presence of 10% FBS. After a 96-hours period of treatment, 20 μl of MTT solution (5 mg/ml in PBS) were added to each well, and the plates were then incubated for 3 hours at 37° C. Medium was then replaced with 100 μl of DMSO per well. Plates were shaken and the optical density was measured at 570 nm using a multiwell plate reader (Bio-Rad, Model 550, Bio-Rad Inc., Hercules, Calif.). Each experiment was performed in triplicate for each drug concentration and was carried out independently at least 3 times. The $IC_{50}$ value was defined as the concentration needed for a 50% reduction in the absorbance calculated based on the survival curves. Response to drug treatment was assessed by standardizing treatment groups to untreated controls. Compounds activity was compared with compound 1. Two compounds 6n and 7d found to be 20 time more potent than compound 1.

Growth Inhibition Results

Growth inhibition of pancreatic cell lines by compound 1 and the compounds 6n, 7d, 6d, 6h, 7b, 6g, 8g, 8h of the present invention are depicted in following FIGS. 8-16, respectively.

Growth Inhibition Assay for Prostate Cancer Cell Lines

This MTT assay was carried using human prostate cancer cell lines CWR22R, LAPC-4 and LnCap using Promega cell titer 96 nonradioactive cell proliferation kit. Cells were trypsinized and centrifuged at 1000 rpm for 5 minutes and the supernatant was aspirated. Cells were resuspended with HBSS to a concentration of 106/ml. Cell suspension was diluted in serum containing medium to plate 2000 cells/well/ 0.2 ml. Cell suspension was transferred to sterile solution basin. Cells were plated using multichannel pipette set at 200 μl and incubated overnight for attachment. One plate was prepared for day 0 MTT assay as follows: 100 μl of media was removed from each well using multichannel pipette and 15 μl of MTT reagent was added. Plates were incubated at 37° C. for 4 hrs. 100 μl of STOP solution was added to each well and incubated at room temperature for 1 hour. Absorbance was measured at 570 and 650 nm on plate reader. All the media from the remaining plates were carefully removed and the cells were treated with the media containing drug. MTT assays were done on days 0, 3, 5 and 7. In the preliminary screening four BPU sulfur analogs 6l, 6h, 6n, 7d and 8h were screened and their activity was compared with compound 1. Two compounds 6n and 7d found to be 20 times more potent compare to compound 1 compound. The data is shown in the following FIGS. 17-34.

Biology. Table 2 (Growth Inhibition of Pancreatic Cancer Cell Lines by BPU and BPTU Analogues ($IC_{50}$)$^a$)compares the cytotoxicity of a series of new derivatives against a panel of seven pancreatic cancer cell lines, as determined by MTT assay. See, Mosmann, T., *J. Immunol. Methods* 65:55-63 (1983).

TABLE 2

| compd | ASPC1 | Panc1 | Panc203 | Panc430 | Panc1005 | Miapaca2 | HS766 |
|---|---|---|---|---|---|---|---|
| 1 | 0.85 | 0.70 | 0.95 | 0.80 | 5.00 | 0.85 | 1.00 |
| 6g | >10 | >10 | 7.50 | 2.00 | >10 | 5.00 | 5.50 |
| 6h | 10.00 | 9.50 | >10 | 7.50 | >10 | 10.00 | 8.50 |
| 6m | 0.77 | 0.68 | >10 | 10.00 | >10 | 0.74 | 0.47 |
| 6n | 1.00 | 0.085 | 0.70 | 0.09 | 10.00 | 0.086 | 0.088 |
| 7b | 6.0 | 7.5 | 5.5 | 6.5 | >10 | 7.0 | 8.0 |
| 7c | 5.20 | 3.50 | >10 | >10 | >10 | 0.92 | 0.27 |
| 7d | 0.45 | 0.09 | 0.085 | 0.20 | 10.00 | 0.095 | 0.70 |
| 8g | 2.50 | 6.50 | 5.50 | 5.50 | 5.50 | 8.00 | 6.50 |
| 8h | >10 | >10 | >10 | >10 | >10 | 6.10 | >10 |

[a]$IC_{50}$ values expressed in µM; Average of three independent experiments.

Of all the tested compounds, compound 6n possessed the highest potency, with $IC_{50}$ values 0.085, 0.09, 0.086, and 0.088 µM against the Panc1, Panc430, Miapaca2, and HS766 cell lines, respectively. Results with compound 7d demonstrated that substitution of $NH_2$ for the $NO_2$ group (6n) in the benzoyl ring did not diminish the cytotoxic activity against the Panc1, Panc203, and Miapaca2 cell lines. Compounds 6n and 7d were 7- to 11-fold more potent than 1 against these cell lines. In the presence of 6m, the growth of cell lines ASPC1, Panc1, Miapaca2, and HS766 was inhibited, with $IC_{50}$ values of 0.77, 0.68, 0.74, and 0.47 µM, respectively.

Cell lines Miapaca2 and HS766 were susceptible to 7c, with $IC_{50}$ values of 0.92 and 0.27 µM, respectively. Compound 8g was effective in inhibiting the growth of all the cell lines, with $IC_{50}$ values ranging from 2.5 to 8.0 µM. For the remaining compounds, the $IC_{50}$ was >10 µM for all the cell lines. Compounds with significant inhibitory activity in pancreatic cancer cells were further evaluated against prostate cancer cell lines in the MTT assay, (Mosmann, T., *J. Immunol. Methods* 65:55-63 (1983)) and the results were compared to those for compound 1 (Table 3). Table 3 demonstrates the growth inhibition of prostate cancer cell lines by BPU and BPTU Analogues $(IC_{50})$[a]

TABLE 3

| compd | CWR22R | LnCaP | LAPC-4 |
|---|---|---|---|
| 1 | 1.00 | 0.50 | 0.25 |
| 6h | >10 | >10 | 6.00 |
| 6l | 5.00 | 0.50 | 0.60 |
| 6m | 5.00 | 1.00 | 0.20 |
| 6n | 0.05 | 0.05 | 0.05 |
| 7c | 2.00 | 0.75 | 0.75 |
| 7d | 0.50 | 0.50 | 0.10 |
| 8h | >10 | 0.50 | 4.00 |

[a]$IC_{50}$ values expressed in µM; Average of three independent experiments. See, Mosmann, T., J. Immunol. Methods 65: 55-63 (1983).

Compound 6n was the most highly potent of the tested compounds, with an $IC_{50}$ of 0.05 µM against all prostate cell lines. It was 5- to 20-fold more potent than compound 1. The CWR22 and LnCap cell lines were equally sensitive ($IC_{50}$) 0.5 µM) to the growth inhibitory effects of 7d. 7c also inhibited cell growth in the prostate cancer cell lines LnCap and LAPC-4 ($IC_{50}$) 0.75 µM).

6n treatment of MCF-7 cells for 48 hours produced rates of apoptosis of 29.7% (10 nM), 51.2% (30 nM), and 53.6% (100 nM), respectively, as compared to 16.1%, 19.5%, and 27.7% for 1 at the same concentration. Apoptosis of MCF-7 cells by 6n and 1 are demonstrated in FIG. 7 and 6n was more potent than 1 in killing MCF-7 cells (Zhu, T., et al., *Cancer Res*, 65:317-324 (2005)).

A mechanism-based tubulin assembly analysis (Hamel, E., *Cell Biochem. Biophys.*, 38:1-22 (2003); and Verdier-Pinard, P., et al, *Mol. Pharmacol*, 53:62-76 (1998)) of four compounds from this series was also conducted. As shown in Table 4, 6n and 6m were effective in inhibiting tubulin assembly, with $IC_{50}$ values of 2.1 and 4.7 µM, respectively. These values were comparable to the $IC_{50}$ of 1.7 µM for the drugs combretastatin and podophyllotoxin, and 2.7 µM for colchicine, which have a similar mechanism of action. Our data indicate (Table 4) that none of our compounds bound to the colchicine binding site on the microtubules.

TABLE 4

Inhibition of Tubulin Polymerization and Colchicine Binding

| compd | tubulin[a] $IC_{50}$ ± SD (µM)± | colchicine binding[b] (% ± SD) |
|---|---|---|
| 6m | 4.7 ± 0.3 | 21 ± 5 |
| 6n | 2.1 ± 0.5 | 17 ± 3 |
| 7c | 36 ± 0.7 | nd c |
| 7d | >40 | nd |
| combretastatin A4 | 1.7 ± 0.2 | 94 ± 5 |
| podophyllotoxin | 1.7 ± 0.1 | 77 ± 8 |
| colchicines | 2.7 ± 0.4 | |

[a]Inhibition of tubulin polymerization. Tubulin was at 10 µM (Hamel, E., Cell Biochem. Biophys., 38: 1-22 (2003)).
[b]Inhibition of [$^3$H]colchicine binding. Tubulin was at 1 µM; both [$^3$H]colchicines and inhibitor were at 5 µM (Verdier-Pinard, P., et al., Mol. Pharmacol, 53: 62-76 (1998)).
c No data.

From Tables 2 and 3, it is interesting to note that the $NO_2$ and $NH_2$ substituents at position 2 of the benzoyl moiety and the Br substituent at position 4 on the pyrimidinyl ring apparently play an important role in the activity of these compounds. Compounds lacking either or both groups displayed weak activity. These findings were in accordance with previously reported structure-activity relationships. See, Okada, H., et al., *Chem. Pharm. Bull.*, 39:2308-2315 (1991); and Gurulingappa, H., et al., *Bioorg. Med. Chem. Lett.*, 14:2213-2216 (2004). In addition, replacement of the urea moiety with thiourea (6g and 6h) had little effect on the activity. Introduction of a sulfide bridge between phenyl and pyrimidinyl rings resulted in higher activity than did an ether link. This variation was observed for compounds 6n and 7d (Tables 2 and 3), both of which showed a significant anticancer effect. For example, an increase in potency of 111-fold for Panc430, 8-fold for Panc1 and Mia-paca2, 14-fold for Panc203, 100-fold for CWR22R, and 20-fold for the LnCap cell line was obtained for compound 6n over 6m. Similarly, when compared to 7c, the activity of 7d was increased by >117-fold for Panc203, 9-fold for Miapaca2, >50-fold for Panc430, 39-fold for Panc1, and 7-fold for the LAPC-4 cell line. A large decrease in the activity of 8g and 8h (when compared to that of 6n) was also seen with the modification of sulfide to sulfoxide and sulfone. Even though 6m and 6n were effective in inhibiting tubulin assembly, their poor binding affinity for colchicine binding site indicates the existence of an alternate binding site mechanism.

In conclusion, the sulfur analogues of BPU of the present invention had excellent growth inhibition activity against both pancreatic and prostate cancer cell lines. 6n and 7d were both found to be more potent than compound 1.

In another aspect, the present invention provides pharmaceutical compositions. The pharmaceutical composition includes a pharmaceutically acceptable excipient and a compound having the formula (I-XXIII):

In one aspect, the present invention provides an antiproliferative, water soluble compound with high bioavailability having the general formula (I)

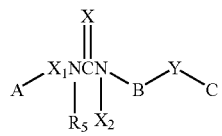

(I)

Where A, B, and C are independently substituted alkyl, cycloalkyl, aryl, heterocycle, or substituted phenyl fused with a saturated or unsaturated 4-to 6-membered rings optionally containing one to three heteroatoms independently selected from N, O, and S; 'X' is oxygen or sulfur; 'Y' is sulfur, sulfoxide or sulfone; $X_1$ is CO or hydrogen; $R_5$ is hydrogen, or alkyl or aryl group; $X_2$ is hydrogen or $SR_6$, wherein $R_6$ is a substituted alkyl, cycloalkyl, aryl, heterocycle, or substituted phenyl fused with a saturated or unsaturated 4-to 6-membered rings optionally containing one to three heteroatoms independently selected from N, O, and S.

The present invention is further defined by compounds having the general formulas (II)-(XIX):

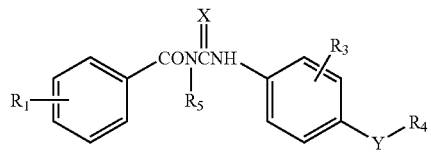

(II)

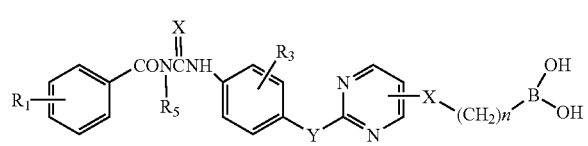

(III)

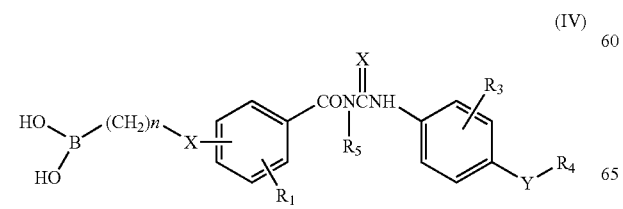

(IV)

Where $R_1$, $R_3$ is H, F, Cl, Br, I, CN, $NO_2$, $NH_2$, NHMe, $NMe_2$, $CF_3$, COOH, CONHOH, alkyl or aryl, group; $R_5$ is alkyl or aryl group; $R_4$ is substituted pyridine, pyrimidine, thiazole, pyrrazole, benzothiozole, indole, benzofuran or any heterocyclic ring; 'X' is oxygen or sulfur; 'Y' is sulfur, sulfoxide or sulfone; n is any integer.

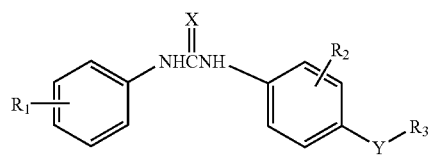

(V)

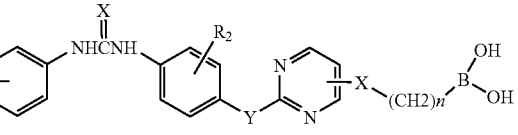

(VI)

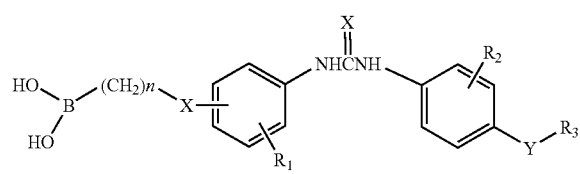

(VII)

Where $R_1$, $R_2$ is H, F, Cl, Br, I, CN, $NO_2$, $NH_2$, NHMe, NMe2, $CF_3$, COOH, CONHOH, alkyl or aryl, group; $R_3$ is substituted pyridine, pyrimidine, thiazole, pyrrazole, benzothiozole, indole, benzofuran or any heterocyclic ring; 'X' is oxygen or sulfur; 'Y' is sulfur, sulfoxide or sulfone; n is any integer.

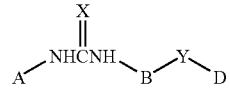

(VIII)

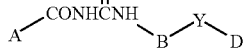

(IX)

Where A, B, and D are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur; 'Y' is sulfur, sulfoxide or sulfone.

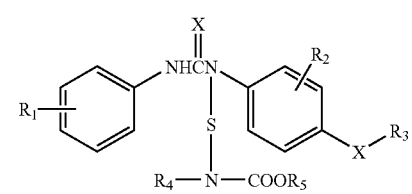

(XII)

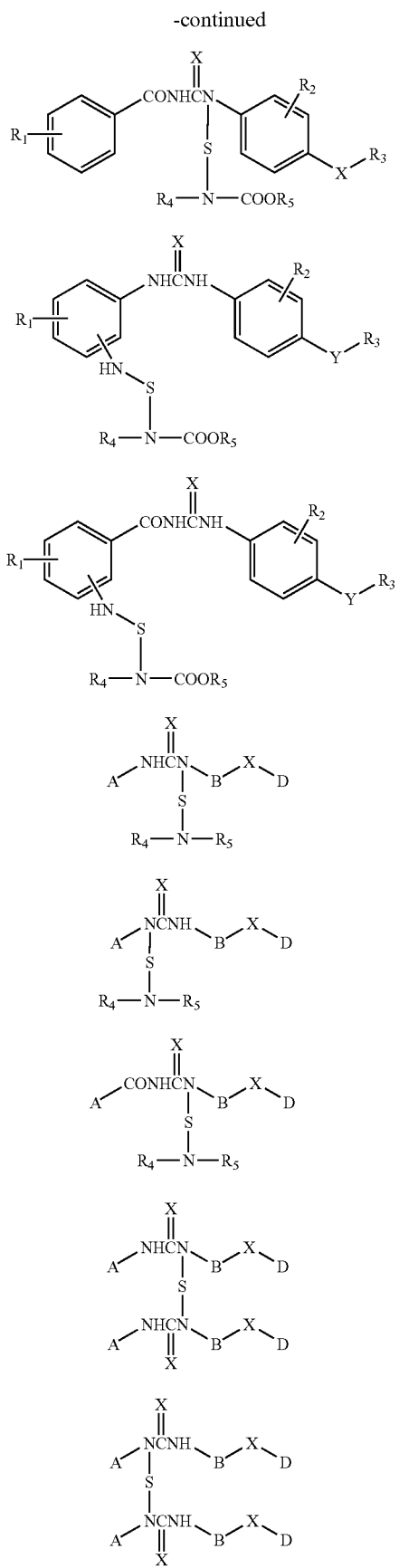
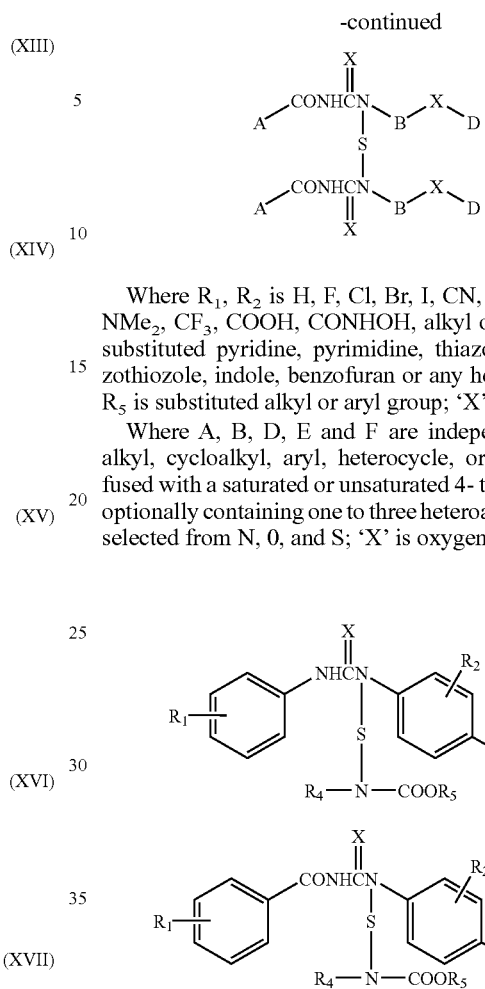

Where $R_1$, $R_2$ is H, F, Cl, Br, I, CN, $NO_2$, $NH_2$, NHMe, $NMe_2$, $CF_3$, COOH, CONHOH, alkyl or aryl, group; $R_3$ is substituted pyridine, pyrimidine, thiazole, pyrrazole, benzothiozole, indole, benzofuran or any heterocyclic ring; $R_4$, $R_5$ is substituted alkyl or aryl group; 'X' is oxygen or sulfur.

Where A, B, D, E and F are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur.

Where A, B, D, E and G are independently substituted alkyl, cycloalkyl, aryl, heterocycle, or substituted phenyl fused with a saturated or unsaturated 4- to 6-membered rings optionally containing one to three heteroatoms independently selected from N, O, and S; 'X' is oxygen or sulfur.

The pharmaceutical compositions described herein are typically used for chemotherapy of various human illnesses, such as but not limited to osteoporesis, psoriasis, kidney failure, and immunosuppressant disorders in a subject in need of such treatment.

In an exemplary embodiment, the pharmaceutical composition includes from 1 to 2000 milligrams of a compound of Formula (I-XXIII). In some embodiments, the pharmaceutical composition includes from 1 to 1500 milligrams of the compound of Formula (I-XXIII). In other embodiments, the pharmaceutical composition includes from 1 to 1000 milligrams of the compound of Formula (I-XXIII).

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally.

Additionally, the compounds of the present invention can be administered transdermally. The compounds of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Thus, the pharmaceutical compositions described herein may be adapted for oral administration. In some embodiments, the pharmaceutical composition is in the form of a tablet. Moreover, the present invention provides pharmaceutical compositions including a pharmaceutically acceptable carrier or excipient and either a compound of Formula (I-XXIII), or a pharmaceutically acceptable salt of a compound of Formula (I-XXIII).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of this invention mixed with a filler or binders such as lactose or starches, lubricants such as talc or magnesium stearate, and, optionally, stabilizers. In soft capsules, the compounds of this invention compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of this invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.,* 281:93-102 (1997). The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of this invention of the invention can be delivered by transdermally, by a topical route, formulated as applicator sticks, solutions, suspensions, emulsions, gels, creams, ointments, pastes, jellies, paints, powders, and aerosols.

The compounds of this invention of the invention can also be delivered as microspheres for slow release in the body. For example, microspheres can be administered via intradermal injection of drug-containing microspheres, which slowly release subcutaneously (see Rao, *J. Biomater Sci. Polym. Ed.*, 7:623-645 (1995); as biodegradable and injectable gel formulations (see, e.g., Gao *Pharm. Res.*, 12:857-863 (1995); or, as microspheres for oral administration (see, e.g., Eyles, *J. Pharm. Pharmacol.*, 49:669-674 (1997). Both transdermal and intradermal routes afford constant delivery for weeks or months.

The compounds of this invention pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compounds of this invention having the formulations of the invention are useful for parenteral administration, such as intravenous (IV) administration or administration into a body cavity or lumen of an organ. The formulations for administration will commonly comprise a solution of the compounds of this invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compounds of this invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, formulations having the compounds of this invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compounds of this invention into the target cells in vivo. (See, e.g., Al-Muhammed, *J. Microencapsul.*, 13:293-306, 1996; Chonn, *Curr. Opin. Biotechnol.*, 6:698-708 (1995); Ostro, *Am. J. Hosp. Pharm.*, 46:1576-1587 (1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

II. Methods for Treating Conditions in Need of Chemotherapy

In still another aspect, the present invention provides a method for the treatment of a disorder or condition which requires chemotherapy. In this method, a subject in need of such treatment is administered an effective amount of a compound having one of the formulae provided above. The amount is effective in treating the illness that the patient is afflicted with.

A variety of disease sates are capable of being treated with chemotherapy. Exemplary disease states include, but are not limited to cancer, kidney failure, osteoporosis, psoriasis, kidney failure, and immunosuppressant disorders. The methods of treatment includes administering to a patient in need of such treatment, a therapeutically effective amount of a compound according to Formula (I-XXIII), or a pharmaceutically acceptable salt thereof.

Thus, in an exemplary embodiment, the present invention provides a method of treating a disorder or condition through chemotherapy, the method including administering to a subject in need of such treatment, an effective amount of a compound of the present invention, such as a compound of Formula (I-XXIII).

The amount of the compounds of this invention adequate to treat a disease is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the rate of absorption, bioavailability, metabolism, clearance, and the like (see, e.g., Hidalgo-Aragones, *J. Steroid Biochem. Mol.*

Biol., 58:611-617 (1996); Groning, *Pharmazie,* 51:337-341 (1996); Fotherby, *Contraception,* 54:59-69 (1996); Johnson, *J. Pharm. Sci.,* 84:1144-1146 (1995); Rohatagi, *Pharmazie,* 50:610-613 (1995); Brophy, *Eur. J. Clin. Pharmacol.,* 24:103-108 (1983); the latest Remington's, supra). The state of the art allows the clinician to determine the dosage regimen for each individual patient, and disease or condition treated.

Single or multiple administrations of formulations having the compounds of this invention can be administered depending on the dosage and frequency as required and tolerated by the patient. The formulations should provide a sufficient quantity of active agent to effectively treat the disease state. Thus, in one embodiment, the pharmaceutical formulations for oral administration of the compounds of this invention is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable formulations having the compounds of this invention will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

After a pharmaceutical composition including a compound of the invention has been formulated in an acceptable carrier, it can be placed in an appropriate container and labeled for treatment of an indicated condition. For administration of the compounds of this invention, such labeling would include, e.g., instructions concerning the amount, frequency and method of administration. In one embodiment, the invention provides for a kit for the treatment of cancer or kidney failure in a human which includes the compounds of this invention and instructional material teaching the indications, dosage and schedule of administration of the compounds of this invention.

III. Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

IV. EXAMPLES

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The discussion below is offered to illustrate certain of the diverse methods available for use in assembling the compounds of the invention. However, the discussion is not intended to define the scope of reactions or reaction sequences that are useful in preparing the compounds of the present invention.

Experimental Section:

Unless otherwise noted, reactions were run in flame-dried round-bottomed flasks under an atmosphere of ultra-high-purity (UHP) argon. All reactive liquid reagents were transferred by syringe or cannula and were added into the flask through a rubber septum. Tetrahydrofuran was freshly distilled from sodium benzophenone ketyl immediately prior to use. All other solvents and reagents were used as received unless otherwise stated. n-BuLi was obtained from commercial sources and was titrated with N-pivaloyl-O-toluidine prior to use. Diethyl ether (ether) and tetrahydrofuran (THF) were distilled from sodium benzophenone ketyl prior to use. Methylene chloride ($CH_2Cl_2$) was distilled from calcium hydride prior to use. All other compounds were purchased from Aldrich Chemical Co. and used without further purification. Analytical thin-layer chromatography (TLC) was conducted with silica gel 60 F254 plates (250 lm thickness; Merck). Column chromatography was performed using short path silica gel (particle size <230 mesh), flash silica gel (particle size 400-230 mesh), or Florisil (200 mesh). Yields are not optimized. Purity of products was judged to be >95% based on their chromatographic homogeneity. High-performance liquid chromatography (HPLC) was carried out with a Rainin HPLX system equipped with two 25 mL/min preparative pump heads using Rainin Dynamax 10 250 mm (semi-preparative) columns packed with 60 A° silica gel (8 lm pore size), either as bare silica or as C-18-bonded silica. Melting points were measured using a Mel-Temp metal-block apparatus and were uncorrected. Nuclear magnetic resonance (NMR) spectra were obtained either on a Varian XL-400 spectrometer, operating at 400 MHz for $^1H$ and 100 MHz for $^{13}C$, or on a Varian XL-500 spectrometer, operating at 500 MHz for $^1H$ and 125 MHz for $^{13}C$. Chemical shifts are reported in parts per million (ppm, δ) downfield from tetramethylsilane (TMS). Multiplicities of signals in the $^1H$ NMR spectra are reported as follows: s (singlet), d (doublet), t (triplet), q (quartet), m (multiplet), dd (doublet of doublets), dt (doublet of triplet), etc.

Infrared spectra were obtained on a Perkin Elmer 1600 FT-IR spectrometer as liquid films and thin layer with NaCl cells. Intensities were reported as s (strong 67-100%), m (medium 34-66%), and w (weak 0-33%) with the following notations, br (broadened), sh (shoulder), etc.

Optical rotations were recorded on JASCO, P-1100 model polarimeter (Japan Spectroscopic Co., Ltd.) with sodium D line at the temperatures as indicated in the experimental section for the specific compounds.

Analytical Thin Layer Chromatography (TLC) was performed on Merck silica gel plates (Merck Kieselgel, 60, 0.25-mm thickness) with $F_{254}$ indicator. Compounds were visualized under UV lamp and/or by developing with iodine, vanillin, p-anisaldehyde or $KMnO_4$ followed by heating with a heat gun. Flash chromatography (Still, W. C., et al., *J. Org. Chem.,* 43:1404 (1978)) was performed as reported by Still and coworkers on 230-400 mesh silica gel (E. M. Science)

with technical and/or HPLC grade solvents. Medium Pressure Liquid Chromatography (MPLC) was performed with FMI pump and prepacked silica gel column (Merck, Labor Columns, LiChroprep Si 60, 40-63 μm). High Pressure Liquid Chromatography (HPLC) was performed on a Rainin HPLX system equipped with two 25 mL pump heads and a Rainin Dynamax UV-C dual-beam variable wavelength detector set at 254 or 260 nm using Phenomenex, Luna 5 μC 18 semipreparative (250×10 mm) column and Chiralcel OJ semipreparative (250×10 mm) column.

Low and high-resolution mass spectra (LRMS and HRMS) were obtained with electronic or chemical ionization (El or CI) either (1) at Johns Hopkins University on a VG Instruments 70-S spectrometer run at 70 eV for EI and run with ammonia ($NH_3$) as a carrier gas for CI or (2) at the Ohio State University on a Finnigan-MAT CH5, a Finnigan-MAT 731, or a VG Instruments 70-VSE spectrometer run at 70 eV for El and run with methane ($CH_4$) for CI.

Example 1

Synthesis of Compounds 6a-n

General Procedure for the Synthesis of Compounds 6a-n. 1-[4-(5-Bromopyrimidin-2-ylsulfanyl)phenyl]-3-(2-nitrobenzoyl)-urea (6n)

A solution of 5-bromo-2-chloropyrimidine (5 g, 0.026 mol), 4-aminothiophenol (3.24 g, 0.026 mol), and $K_2CO_3$ (7.14 g, 0.052 mol) in dry DMSO (50 mL) was stirred at 120 °C. for 2.5 hours under $N_2$. After cooling, the reaction mixture was poured into water and extracted with ethyl acetate. The organic layer was washed with water and saturated brine and then dried. The solvent was evaporated to give a residue that was purified by silica gel flash column chromatography (ethyl acetate-hexane 1:3) to give 4-(5-bromopyrimidin-2-ylsulfanyl)phenylamine (4n), yield 74%. $^1$H NMR (400 MHz, $CDCl_3$): δ 8.51 (s, 2H), 7.37 (d, J) 8.0 Hz, 2H), 6.72 (d, J) 8.0 Hz, 2H), 2.63 (s, 2H); EI-MS m/z 281 [M]$^+$, 283 [M+2]$^+$.

A solution of 2-nitrobenzoyl isocyanate (3 g, 0.016 mol) in dry 1,4-dioxane (15 mL) was added dropwise to a solution of 4n (2.93 g, 0.01 mol) in dry 1,4-dioxane (15 mL) with stirring at room temperature. The reaction mixture was stirred for 18 hours and then diluted with water. The precipitated solid was collected by filtration and washed with water. The solid was dissolved in ethyl acetate, and the organic layer was washed with water 2-3 times, dried, and concentrated to give 1-[4-(5-bromopyrimidin-2-ylsulfanyl)-phenyl]-3-(2-nitrobenzoyl) urea (6n), yield 92%. $^1$H NMR (400 MHz, DMSO-$d_6$): δ 11.32 (br, s, 1H), 10.35 (br, s, 1H), 8.78 (s, 2H), 8.22 (m, 1H), 7.91 (m, 1H), 7.77 (m, 2H), 7.67 (m, 2H), 7.57 (m 2H); EI-MS m/z 473 [M]$^+$, 475 [M+2]$^+$; HRMS calculated for $C_{18}H_{12}BrN_5O_4SNa$ [M+Na]$^+$:495.9685, found: 495.9701. Anal. ($C_{18}H_{12}BrN_5O_4S$) C, H, N.

Example 2

Synthesis of Compounds 7a-d

General Procedure for the Synthesis of Compounds 7a-d. 1-(2-Aminobenzoyl)-3-[4-(5-bromopyrimidin-2-ylsulfanyl) phenyl]urea (7d)

Iron powder (1.77 g, 31.63 mmol) was added in portions to a mixture of 6n (3 g, 6.32 mmol) in AcOH (90 mL) at 80° C. The reaction mixture was refluxed for 30 min and then cooled to room temperature and diluted with water. The precipitated solid was collected by filtration. The solid was dissolved in an excess of ethyl acetate and filtered. The filtrate was dried and concentrated to give a residue that was purified by silica gel flash column chromatography (ethyl acetate-hexane 2:3) to give 7d, yield 62%. $^1$H NMR (400 MHz, DMSO-$d_6$): δ 11.92 (br, s, 1H), 10.73 (br, s, 1H), 8.75 (s, 2H), 7.68 (m, 2H), 7.57 (m, 2H), 7.25 (m, 1H), 6.79 (m, 1H), 6.59 (m 2H); EI-MS m/z 443 [M]$^+$, 445 [M+2]$^+$; HRMS calculated for $C_{18}H_{12}BrN_5O_2SNa$ [M+Na]$^+$: 465.9943, found: 465.9938. Anal. ($C_{18}H_{14}BrN_5O_2S$) C, H, N.

Example 2

Synthesis of Compounds 8a-h

General Procedure for the Synthesis of Compounds 8a-h. 1-[4-(5-Bromopyrimidine-2-sulfinyl)phenyl]-3-(2-nitrobenzoyl)-urea (8g).

To a stirred solution of 6n (1.0 g, 2.11 mmol) in DCM (50 mL) at 0° C. was added MCPBA (0.364 g, 2.11 mmol) in portions. The resulting mixture was stirred at room temperature for 6 h and then diluted with water and made slightly basic with $Na_2CO_3$ solution. The DCM layer was separated, and the aqueous layer was extracted with DCM. The combined organic layers were dried and evaporated to give a residue that was purified by silica gel flash column chromatography (ethyl acetate-methanol 5:1) to give 8g, yield 48%. $^1$H NMR (400 MHz, DMSO-$d_6$): δ 11.32 (br, s, 1H), 10.38 (br, s, 1H), 9.15 (s, 2H), 8.20 (m, 1H), 7.88 (m, 1H), 7.72-7.80 (m, 6H); EI-MS m/z 489 [M]$^+$, 491 [M+2]$^+$; HRMS calculated for $C_{18}H_{12}BrN_5O_5SNa$ [M+Na]$^+$: 511.9634, found: 511.9632. Anal. ($C_{18}H_{12}BrN_5O_5S$) C, H, N.

1-[4-(5-Bromopyrimidine-2-sulfonyl)phenyl] -3-(2-nitrobenzoyl)-urea (8h)

The title compound was synthesized from 6n according to above procedure using 3 equiv of MCPBA, yield 56%. $^1$H NMR (400 MHz, DMSO-$d_6$): δ 11.42 (br, s, 1H), 10.55 (br, s, 1H), 9.23 (s, 2H), 8.21 (m, 1H), 7.76-7.97 (m, 7H); EI-MS m/z 505 [M]$^+$, 507 [M+2]$^+$; HRMS calculated for $C_{18}H_{12}BrN_5O_6SNa$ [M+Na]$^+$: 527.9583, found: 527.9592. Anal. ($C_{18}H_{12}BrN_5O_6S$) C, H, N.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the compounds of this invention are equally applicable to the methods of treating disease states described herein. All publications, patents, and patent applications cited herein are hereby incorporated by reference in their entirety for all purposes.

What is claimed is:

1. A compound represented by either of the following formulas:

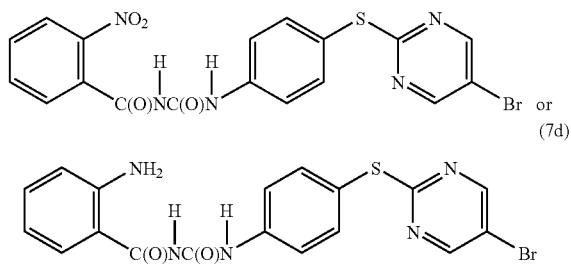

or a pharmaceutically acceptable salt thereof.

2. A compound represented by the following formula:

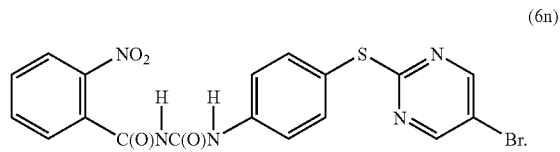

3. A compound represented by the following formula:

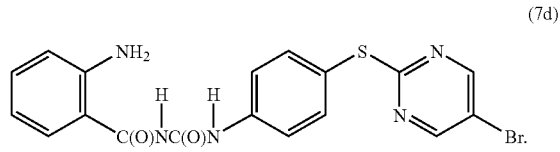

4. A pharmaceutical composition comprising a pharmaceutically acceptable excipient and a compound according to claim 1.

5. A pharmaceutical composition comprising a pharmaceutically acceptable excipient and a compound according to claim 2.

6. A pharmaceutical composition comprising a pharmaceutically acceptable excipient and a compound according to claim 3.

7. A method of treating a subject afflicted with prostate cancer or pancreatic cancer, said method comprising administering an effective amount of a compound according to claim 1, or a pharmaceutically acceptable salt thereof, optionally in a composition comprising a pharmaceutically acceptable excipient.

8. A method of treating a subject afflicted with prostate cancer or pancreatic cancer, said method comprising administering an effective amount of a compound according to claim 2, optionally in a composition comprising a pharmaceutically acceptable excipient.

9. A method of treating a subject afflicted with prostate cancer or pancreatic cancer, said method comprising administering an effective amount of a compound according to claim 3, optionally in a composition comprising a pharmaceutically acceptable excipient.

10. A method of inhibiting growth of a pancreatic cancerous cell or a prostate cancerous cell, comprising contacting said pancreatic cancerous cell or said prostate cancerous cell with a composition comprising 1 nM to 10 microM of a compound according to claim 1. or a pharmaceutically acceptable salt thereof.

11. A method of inhibiting growth of a pancreatic cancerous cell or a prostate cancerous cell, comprising contacting said pancreatic cancerous cell or said prostate cancerous cell with a composition comprising 1 nM to 10 microM of a compound according to claim 2 or a pharmaceutically acceptable salt thereof.

12. A method of inhibiting growth of a pancreatic cancerous cell or a prostate cancerous cell, comprising contacting said pancreatic cancerous cell or said prostate cancerous cell with a composition comprising 1 nM to 10 microM of a compound according to claim 3, or a pharmaceutically acceptable salt thereof.

* * * * *